US008178331B2

(12) United States Patent
Gasch et al.

(10) Patent No.: US 8,178,331 B2
(45) Date of Patent: May 15, 2012

(54) RECOMBINANT YEAST WITH IMPROVED ETHANOL TOLERANCE AND RELATED METHODS OF USE

(75) Inventors: Audrey P. Gasch, Madison, WI (US); Jeffrey A. Lewis, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/232,327

(22) Filed: Sep. 14, 2011

(65) Prior Publication Data

US 2012/0064591 A1 Mar. 15, 2012

Related U.S. Application Data

(60) Provisional application No. 61/383,185, filed on Sep. 15, 2010, provisional application No. 61/484,260, filed on May 10, 2011.

(51) Int. Cl.
*C12P 7/06* (2006.01)
*C07H 21/04* (2006.01)
*C12N 1/00* (2006.01)
(52) U.S. Cl. ............ 435/161; 435/254.2; 536/23.2
(58) Field of Classification Search .......... 536/23.2; 435/161, 254.2
See application file for complete search history.

(56) References Cited

U.S. PATENT DOCUMENTS 7,314,974 B2 * 1/2008 Cao et al. ............ 800/289

OTHER PUBLICATIONS

Solomon, B.D. (2010) Biofuels and sustainability. Ann NY Acad Sci 1185:119-134.
Alper, H., et al. (2006) Engineering yeast transcription machinery for improved ethanol tolerance and production. Science 314:1565-1568.
Stanley, D., et al. (2010) The ethanol stress response and ethanol tolerance of *Saccharomyces cerevisiae*. J Appl Microbial 109:13-24.
Fujita, K., Matsuyama, A., Kobayashi, Y.,lwahashi, H. (2006) The Genome-wide screening of yeast deletion mutants to the genes required for tolerance to ethanol and other alcohols. FEMS Yeast Res 6:744-750.
Teixeira, M. C., et al. (2009) Genome-wide identification of *Saccharomyces cerevisiae* genes required for maximal tolerance to ethanol. Appl. Environ. Microbial. 75:5761-5772.
van Voorst, F., et al. (2006) Genome-wide identification of genes required for growth of *Saccharomyces cerevisiae* under ethanol stress. Yeast 23:351-359.
Yoshikawa, K., et al. (2009) Comprehensive phenotypic analysis for identification of genes affecting growth under ethanol stress in *Saccharomyces cerevisiae*, FEMS Yeast Res 9:32-44.
Kubota S. et al. (2004) Effect of ethanol on cell growth of budding yeast: genes that are imporant for cell growth in the presence of ethanol. Biosci. Biotechnol. Biochem. 68:968-972.

Alexandre, H., Ansanay-Galeote, V., Dequin, S.,Blondin, B. (2001) Global gene expression during short-term ethanol stress in *Saccharomyces cerevsiae*. FEBS Lett 498:98-103.
Fujita, K., Matsuyama, A., Kobayashi, Y., Iwahashi, H. (2004) Comphrensive gene expression analysis of the response to straight-chain alcohols in *Saccharomyces cerevisiae* using cDNA microarray. J Appl Microbiol 97: 57-67.
Chandler, M., Stanley, G. A., Rodgers, P.,Chambers, P. (2004) A genomic approach to defining the ethanol stress response in the yeast *Saccharomyces cerevisiae*. Ann Microbial 54:427-545.
Hirasawa, T., et al. (2007) Identification of target genes conferring ethanol stress tolerance to *Saccharomyces cerevisiae* based on DNA microarray data analysis. J Biotechnol 131:34-44.
Berry, D.B., Gasch, A.P. (2008) Stress-activated genomic expresssion changes serve a preparative role for impending stress in yeast. Mol Biol Cell 19:4580-4587.
Rossignol, T., Dulau, L., Julien, A.,Blondin, B. (2003) Genome-wide monitoring of wine yeast gene expression during alcoholic fermentation. Yeast 20:1369-1385.
Wu, H., et al. (2006) Global gene expression analysis of yeast cells during sake brewing. Appl Environ l'Microbiol 72:7353-7358.
Cavalieri, D., Townsend, J. P.,Hartl, D. L. (2000) Manifold anomalies in gene expression in a vineyard isolate of *Saccharomyces cerevisiae* revealed by DNA microarray analysis. Proc Natl Aced Sci U S A 97:12369-12374.
Fay, J.C., McCullough, H.L., Sniegowski, P.D., Eisen, M.B. (2004) Population genetic variation in gene expression is associated with phenotypic variation in *Saccharomyces cerevisiae* . Genome Biol 5:R26.
Kvitek, D.J., Will, J.L.,Gasch, A. P. (2008) Variations in stress sensitivity and genomic expression in diverse *S. cerevisiae* isolates. PLoS Genet 4:e1000223.
Mortimer, R. K., Johnston, J. R. (1986) Genealogy of principal strains of the yeast genetic stock center. Genetics 113:35-43.
Gasch, A. P., et al. (2000) Genomic expression programs in the response of yeast cells to environmental changes. Mol Biol Cell 11:4241-4257.
Gaisne, M., Becam, A.M., Verdiere, J., Herbert, C.J. (1999) A 'natural' mutation in *Saccharomyces cerevisiae* strains derived from S288c affects the complex regulatory gene HAP1 (CYP1). Curr Genet 36:195-200.
Watanabe, M., Watanabe, D., Akao, 71.,Shimoi, H. (2009) Overexpression of MSN2 in a sake yeast strain promotes ethanol tolerance and increases ethanol production in sake brewing. J Biosci Bioeng 107:516-518. You, K. M., Rosenfield, C. L., Knipple, D. C. (2003) Ethanol tolerance in the yeast *Saccharomyces cerevisiae* is dependent on cellular oleic acid content. Appl Environ Microbiol 69:1499-1503.
Meaden, P.G., et al. (1999) Endocytosis and vacuolar morphology in *Saccharomyces cerevisiae* are altered in response to ethanol stress or heat shock. Yeast 15:1211-1222.
Lucero, P., Penalver, E., Moreno, E., Lagunas, R. (2000) Internal trehalose protects endocytosis from inhibition by ethanol in *Saccharomyces cerevsiae*. Appl. Environ. Microbial. 66:4456-4461.
Singer, M, A., Lindquist, S. (1998) Multiple effects of trehalose on protein folding in vitro and in vivo. Mol Cell 1;639-648.

(Continued)

*Primary Examiner* — Maryam Monshipouri
(74) *Attorney, Agent, or Firm* — Quarles & Brady LLP

(57) ABSTRACT

The present invention provides isolated Elo1 and Mig3 nucleic acid sequences capable of conferring increased ethanol tolerance on recombinant yeast and methods of using same in biofuel production, particularly ethanol production. Methods of bioengineering yeast using the Elo1 and, or, Mig3 nucleic acid sequences are also provided.

21 Claims, 14 Drawing Sheets
(11 of 14 Drawing Sheet(s) Filed in Color)

OTHER PUBLICATIONS

Walker-Caprioglio, H.M., Casey, W.M., Parks, L.W. (1990) *Saccharomyces cerevisiae* membrane sterol modifications in response to growth in the presence of ethanol. Appl Environ Microbiol 56:2853-2857.

Lu, A., Hirsch, J. P. (2005) Cyclic AMP-independent regulation of protein kinase A substrate phosphobilation by Kelch repeat proteins. Eukaryot. Cell 4:1794-1800.

Sopko, R., et al. (2006) Mapping pathways and phenotypes by systematic gene overexpression. Mol Cell 21:319-330.

Gasch, A. P. (2002) Yeast genomic expression studies using DNA microarrays. Methods Enzymol 350:393-414.

Open Biosystems 2008. Yeast GST Manual, Document SS051497, in Yeast GST Fusion Collection and Strains; Catalog Nos. YSC4423 & YSC4515. Huntsville, AL.

Valadi, H., A. Valadi, R. Ansell, L. Gustafsson, L. Adler, J. Norbeck, and A. Eilomberg. 2004. NADH-reductive stress in *Saccharomyces cerevisiae* induces the expression of the minor isoform of glyceraldehyde-3-phosphate dehydrogenase (TDH1). Curr Genet 45:90-95.

Gonnet, G.H., M.A. Cohen, and S.A. Benner. 1992. Exhaustive matching of the entire protein sequence database. Science 256:1443-1445.

Piper, P. W. 1995. The heat shock and ethanol stress responses of yeast exhibit extensive similarity and functional overlap. FEMS Microbiol. Lett. 134:121-127.

Lyne, R., G. Burns.J, Mate, C. J. Penkett, G. Rustici, D. Chen, C. Langford, D. Vetrie, and J. Bahler. 2003. Whole-genome microarrays of fission yeast: characteristics, accuracy, reproducibility, and processing of array data. BMC Genomics 4:27.

Lutfiyya, L. L., V. R. Iyer, J. DeRisi, M. J. DeVit, P. O. Brown, and M. Johnston. 1998. Characterization of three related glucose repressions and genes ther regulate in *Saccharomyces cerevisiae*. Genetics 150:1377-1391.

Lewis, J. A., I. M. Elkon, M. A. McGee, A. J. Higbee, and A. P. Gasch, 2010, Exploiting natural variation in *Saccharomyces cerevisiae* to identify genes for increased ethanol resistance. Genetics 186:1197-1205.

Dubacq, C., A. Chevalier, and C. Mann. 2004. The protein kinase Snf1 is required for tolerance to the ribonucleotide reductase inhibitor hydroxyurea. Mol Cell Biol 24:2560-2572.

* cited by examiner

```
Mig3                                    ------------------------MNYLRDKFPPDRDQ-RPFRCEICSRGFHRLEHKKRHGRTH  39
Mig2                                    ------------------------MPKRQTRFPVDREN-RPFRCDTCHRGFHRLEHKKRHLRTH  39
Mig1                                    MQSPYPMTQVSHVDGGSLLKESKSKSKVAAKSEAPRPHACFICHRAFHRLERQTRHMRIH      60
                                                                : ..: .,:    **,. *  * *,*******,.** * *

Mig3                                    TGEKPHKCTVQGCPKSFSRSDELKRHLRTHTKGVQR---RRIKKGSRKTVVRTATAAPTTF    97
Mig2                                    TGEKPHHCAFPGCGRSFSRSDELKRHMRTHTGQSQR---RLRKASVQKQEFLTVSGIPTIA    97
Mig1                                    TGEKPHACDFPSCVRKFSRSDELTRHRRIHTNSHPRGKRGRKRKVVGSPIRSASSSATSI   120
                                        ******  .  .* *********,**  *  **            *       , ,,,. *

Mig3                                    NEN---TGVSLTGIQQSKVPPILISVAQNCDDVN--------------IRNTGRHSGIYET-   141
Mig2                                    SG---------VHIRQPIPQVLPANMAINVQAVN--------------GGNIIRAPRAVHP-   135
Mig1                                    PDLNTAHYSPPLPQQHLSPLIPIAIAPKEHSGRSSTRKGRKTKFEIGESGGSDPYMVSSP    160
                                                  *      :  :* : :  .                    :     *  .

Mig3                                    ----QAPAILVPVINIPNDPHPIPSSLSTTSITSIASVYF-STSPFQYL------RSGFPK   191
Mig2                                    ----MVIPIMAQPAPIRASAASFQPATSPMPISTYTPVPSQSFTSFQSS------IGSIQS   186
Mig1                                    KTMAKIPVSVEPPPSLALHMMSYQTSSASTALSSLERSHSGSRLKLRALSSLQMRTPIAS   240
                                               :   :  *    :  :   : . :*:::  :        **       :  .

Mig3                                    DPASTPYVHSSGSSIALGELSSNSSIFSKGRRHLAANSGPDSLSGS-RNQSSASLLSQTS   250
Mig2                                    NSDVSSIFSHMNVRVHTPRSVPRSPRDGYLRQQHIPQQYQRQTASP-SVARQQKTFARSL   245
Mig1                                    SAPRTVFIDGPEQKQLQQQQHSLSPRYSNTVILPRPRSLTDFQGLMNANPRNHGSLRAQT   300
                                          .    .   .    :   . .. :    *     .    .

Mig3                                    HPSKSFSRPFTDLSPLRRIMPSVRTGDHEI---------------------------------   289
Mig2                                    ASALSTLQRKTPVSAPSTTIESPSSPSDSS---------------------------------   273
Mig1                                    QSSVQLKRPSSVLSLNDLLVGQRNTNESDSDPTTGEDEREDGLRDFSRSSIDRLEQDYLQ   360
                                         .:  .  :    *      .        *

Mig3                                    --SRTVSVSSSGSSLTSVTYQDTAARDMGNGIFFDRPPYTQKAC------KSHRKYKVHAV   333
Mig2                                    --STSASSSAISLPFSNAFSQLAVAKELES-VYLDSNRYTTKTR------KERAKFEIPEE   327
Mig1                                    EQSRKKSKTSTPTTHLSRSTSGTRLSTLGFVRHQRHLHFSGSSPDFQKELHSRLLNVQQQ   420
                                            .*  :::  . . .   :          :  :                :        ::

Mig3                                    SRGRQHSRAQFHISGDOEDSNVRQESRAS---------------------NTSPNVSLPPIKSI   377
Mig2                                    Q--RSDTHHSSGSHKRKHRSLRHRSKSR-----------------------KKLSGVKLPPVRHL   369
Mig1                                    QQEQHTLLQSQHTSHQSQHQNQNQMMASSSSLSTTFLLLSPRVRHIHTAISTQQTFISQS   480
                                                             *.:.*.:,.  :: : :                  :.  ...  .*:  .

Mig3                                    LRQIDNFRSAPSYYSK---------  393            SEQ ID NO: 1
Mig2                                    LKQIDVFRGPKRV------------  382            SEQ ID NO: 2
Mig1                                    DSQVQELETLPPIKSLFLPFPHM   503              SEQ ID NO: 3
                                        *::  :  :

Fig. 14
```

RECOMBINANT YEAST WITH IMPROVED ETHANOL TOLERANCE AND RELATED METHODS OF USE

CROSS-REFERENCE TO RELATED APPLICATION

This application claims the benefit of U.S. Provisional Patent Application No. 61/383,185, filed Sep. 15, 2010 and U.S. Provisional Patent Application No. 61/484,260, filed May 10, 2011, each of which is incorporated herein by reference as if set forth in their entirety.

STATEMENT AS TO RIGHTS TO INVENTIONS MADE UNDER FEDERALLY SPONSORED RESEARCH AND DEVELOPMENT

This invention was made with government support under DE-FC02-07ER64494 awarded by the US Department of Energy. The government has certain rights in the invention.

FIELD OF THE INVENTION

The present invention relates to materials and methods for the production of ethanol. More particularly, the present invention relates to genes for providing increased ethanol tolerance in yeast, recombinant yeast with improved ethanol tolerance, and methods for using same for enhanced ethanol production.

BACKGROUND OF THE INVENTION

Cellulosic materials are an attractive source for biofuel production, given the availability of agricultural residues that do not directly compete with food sources. However, fermentation of cellulosic biomass is problematic. Stressful byproducts generated during pre-processing, coupled with the unique composition of pentose and hexose sugars, limit microbial ethanol production. Significant attention is therefore being dedicated towards engineering stress tolerance microbes for cellulosic fermentation. *Saccharomyces cerevisiae* has been the organism of choice for ethanol production, because of its inherent ethanol tolerance. However, high ethanol levels can still inhibit viability and fermentation, and engineering greater ethanol resistance is therefore an important step for improved bioethanol production.

Ethanol affects many cellular processes, including membrane fluidity, protein stability, and energy status. Recent genetic screens have implicated additional genes important for ethanol tolerance, including those involved in vacuolar, peroxisomal and vesicular transport, mitochondrial function, protein sorting, and aromatic amino acid metabolism. Despite the attention to the mechanism of ethanol tolerance, significant gaps in understanding this important mechanism still exist. Several studies have investigated the global gene expression response to ethanol. However, mutational analysis shows that most genes up-regulated by ethanol are not required for ethanol tolerance. Thus, gene expression responses in a single strain are poor predictors of genes important for tolerance of the initial stressor. The inventors maintain that the role of stress dependent gene expression changes is not to survive the initial stress, but rather to protect cells against impending stress in a phenomenon known as acquired stress resistance. When cells are pretreated with a mild stress, they often acquire tolerance to what would otherwise be a lethal dose of the same or other stresses. Consistently, the gene expression response triggered by a single stress treatment has no impact on surviving the initial stress, but instead is critical for the increased resistance to subsequent stress. However, it remains true that relatively few of the previously-observed expression changes are important for subsequent tolerance of a particular stress.

Furthermore, the field's understanding of the physiological and transcriptional response to ethanol has been further narrowed since most studies focus on laboratory derived strains. While ethanol tolerance and adaptation have been explored in sake, wine, and industrial yeast strains, investigators have only recently begun to appreciate the physiological diversity of natural yeast isolates. Wild yeast isolates from diverse environments have widely varying phenotypes under various conditions, and many of these phenotypes may be related to variation in gene expression.

Thus, it can be appreciated that identifying genes related to ethanol tolerance has posed a substantial challenge to the field. Accordingly, a need exists in the field to identify genes that influence ethanol tolerance in yeast, and consequently engineer recombinant strains of yeast capable of increased ethanol yields.

SUMMARY OF THE INVENTION

The present invention is largely related the inventors' research efforts to determine yeast strain-specific differences in the physiological and transcriptional response to ethanol. The inventors compared strains with and without the ability to acquire increased ethanol tolerance after ethanol pretreatment, then identified corresponding gene expression differences across strains. This strategy revealed genes involved in acquired ethanol tolerance, and identified genes that increase ethanol tolerance when over expressed. By applying systems biology approaches to the analysis of phenotypic diversity, the inventors have identified key genes involved in ethanol tolerance.

In a first aspect, the present invention provides an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid.

In some embodiments of the first aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In a second aspect, the present invention provides a recombinant vector comprising an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid.

In some embodiments of the second aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In a third aspect, the present invention provides a recombinant yeast comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid.

In some embodiments of the third aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In preferred embodiments of the third aspect, the recombinant yeast according to the invention is of the genus *Saccharomyces*, more preferably of the species *Saccharomyces cerevisiae*. In some preferred embodiments, the recombinant yeast is of the *Saccharomyces cerevisiae* strain CEN.PK, PE-2, BG-1, CAT-1, SA-1, VR-1 or JAY270. In certain embodiments of the third aspect, the nucleic acid contained in the recombinant yeast is a portion of an extrachromosomal vector stably maintained in the recombinant yeast. In alternative embodiments, the nucleic acid is integrated into a chromosome of the recombinant yeast.

In a fourth aspect, the present invention provides a yeast inoculum, comprising: a recombinant yeast comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid; and a culture medium.

In some embodiments of the fourth aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In preferred embodiments of the fourth aspect, the recombinant yeast according to the invention is of the genus *Saccharomyces*, more preferably of the species *Saccharomyces cerevisiae*. In some preferred embodiments, the recombinant yeast is of the *Saccharomyces cerevisiae* strain CEN.PK, PE-2, BG-1, CAT-1, SA-1, VR-1 or JAY270. In certain embodiments of the third aspect, the nucleic acid contained in the recombinant yeast is a portion of an extrachromosomal vector stably maintained in the recombinant yeast. In alternative embodiments, the nucleic acid is integrated into a chromosome of the recombinant yeast.

In other embodiments of the fourth aspect, the yeast inoculum, comprising: (a) a recombinant yeast overexpressing Elo1 or a polypeptide substantially identical to Elo1 that is capable of enzymatic elongation of fatty acids, wherein said overexpression confers increased ethanol tolerance on the recombinant yeast relative to a control yeast lacking the overexpression; and (b) a culture medium. Preferably, overexpression of Elo1 or the enzyme substantially identical to Elo1 is under inducible control of an inducible promoter operably linked to the nucleic acid encoding Elo1 or the enzyme substantially identical to Elo1.

In a fifth aspect, the present invention provides a method for producing ethanol from a recombinant yeast. Such a method includes steps of: culturing under ethanol-producing conditions a recombinant yeast that comprises: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid; and isolating ethanol produced by the recombinant yeast.

In certain embodiments of the fifth aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In preferred embodiments of the fifth aspect, the recombinant yeast according to the invention is of the genus *Saccharomyces*, more preferably of the species *Saccharomyces cerevisiae*. In some preferred embodiments, the recombinant yeast is of the *Saccharomyces cerevisiae* strain CEN.PK, PE-2, BG-1, CAT-1, SA-1, VR-1 or JAY270. In certain embodiments of the third aspect, the nucleic acid contained in the recombinant yeast is a portion of an extrachromosomal vector stably maintained in the recombinant yeast. In alternative embodiments, the nucleic acid is integrated into a chromosome of the recombinant yeast.

In certain embodiments of the fifth aspect, at least a portion of the culturing step takes place in a culture medium having an ethanol concentration of greater than about 15% (v/v). In yet other embodiments, at least a portion of the culturing takes place in a culture medium having an ethanol concentration of greater than about 20% (v/v).

In a sixth aspect, the present invention encompasses a method of providing a recombinant yeast useful in ethanol production, comprising introducing into an isolated yeast an isolated nucleic acid comprising (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid, thereby providing a recombinant yeast capable of increased ethanol tolerance relative to a control yeast lacking said isolated nucleic acid.

In certain embodiments of the sixth aspect, a heterologous promoter is operably linked to the isolated nucleic acid. In certain of these embodiments, the heterologous promoter is the ACT1, PGK1, TDH3, TEF1, TEF2, GAL4, CUP1, PHO5, or tetO7 promoter. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In preferred embodiments of the sixth aspect, the recombinant yeast according to the invention is of the genus *Saccharomyces*, more preferably of the species *Saccharomyces cerevisiae*. In some preferred embodiments, the recombinant yeast is of the *Saccharomyces cerevisiae* strain CEN.PK, PE-2, BG-1, CAT-1, SA-1, VR-1 or JAY270. In certain embodiments of the third aspect, the nucleic acid contained in the recombinant yeast is a portion of an extrachromosomal vector stably maintained in the recombinant yeast. In alternative embodiments, the nucleic acid is integrated into a chromosome of the recombinant yeast.

In certain embodiments of the sixth aspect, at least a portion of the culturing step takes place in a culture medium having an ethanol concentration of greater than about 15% (v/v). In yet other embodiments, at least a portion of the culturing takes place in a culture medium having an ethanol concentration of greater than about 20% (v/v).

In a seventh aspect, the invention provides recombinant yeast strains provided by the method of the fifth aspect of the invention.

In an eighth aspect, the invention provides recombinant yeast strains according to the third aspect of the invention for use in ethanol production. In certain preferred embodiments, recombinant *Saccharomyces cerevisiae* strains include the strain BY4741/pEGH(ELO1), in other preferred embodiments recombinant *Saccharomyces cerevisiae* strains include the strain BY4741/pEGH(MIG3).

As can be appreciated, the present invention contemplates the use of recombinant yeast as described herein for use in the production of ethanol, including certain exemplary recombinant *Saccharomyces cerevisiae* strains specifically identified herein.

This invention provides the advantage over prior ethanol-producing technologies in that embodiments of the invention utilize or are based on a robust recombinant DNA approach that provides yeast strains with increased ethanol tolerance. Other objects, features and advantages of the present invention will become apparent after review of the specification, claims and drawings. The detailed description and examples enhance the understanding of the invention, but are not intended to limit the scope of the appended claims.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 14 depicts a Clustal W alignment of Mig1, Mig2, and Mig3. Identical matches are denoted by "*", strong similarity is denoted by ":", and weak similarity is denoted by ".". The "strong" and "weak" similarity groups were determined using the Gonnet Pam250 matrix (strong similarity=score>0.5, weak similarity=a positive score≦0.5) (Gonnet, G. H., M. A. Cohen, and S. A. Benner. 1992. Exhaustive matching of the entire protein sequence database. Science 256:1443-1445, incorporated herein by reference as if set forth in its entirety).

DETAILED DESCRIPTION OF THE INVENTION

I. In General

Figure 1:
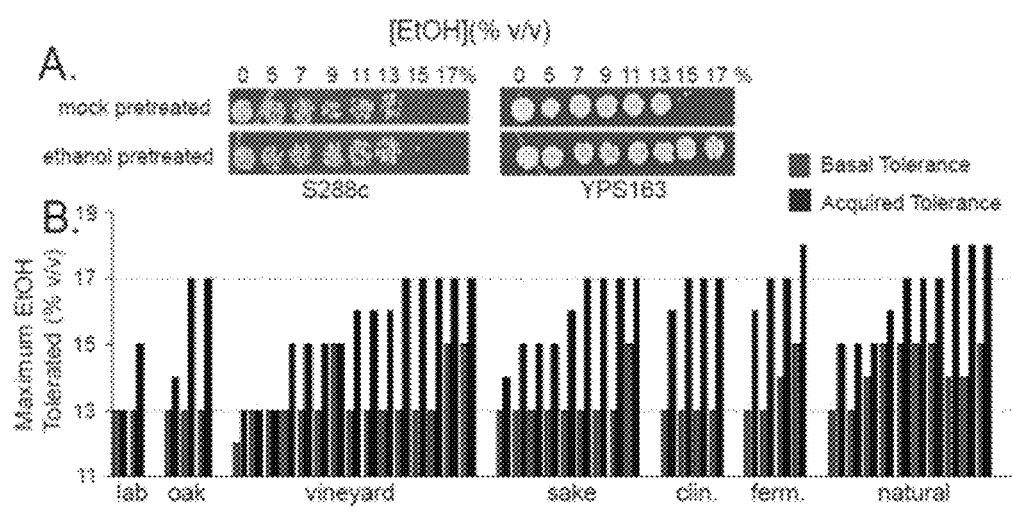
FIG. 1 depicts acquired ethanol tolerance in diverse yeast strains. A) A representative acquired ethanol tolerance assay is shown. S288c (left) or YPS163 (right) was exposed to 5% ethanol or mock pretreatment for 60 min. Cells were exposed to one of seven indicated severe dose of ethanol for 2 hours and then plated onto a YPD plate to score viability. B) Basal (orange) and acquired (blue) percent ethanol tolerated is shown for strains collected from diverse niches ('clin'=clinical, 'ferm'=fermentations). The maximal dose survived was based on >50% spot density compared to the no-ethanol control. Data represent the average of biological duplicates. Strains and scores are found in Dataset S1.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986); each incorporated herein by reference as if set forth in its entirety.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". Promoters which allow the selective expression of a gene in most cell types are referred to as "inducible promoters".

A "host cell" is a cell which has been transformed or transfected, or is capable of transformation or transfection by an exogenous polynucleotide sequence. A host cell which has been transformed or transfected may be more specifically referred to as a "recombinant host cell". Preferred host cells for use in methods of the invention include yeast cells, particularly yeast cells of the genus *Saccharomyces*, more preferably of the species *Saccharomyces cerevisiae*.

As used herein, the term "Elo1 polypeptide" refers to the polypeptide set forth in SEQ ID NO:1. The Elo1 amino acid sequence is publicly available under GenBank accession number NP_012339. An exemplary nucleic acid sequence encoding the Elo1 polypeptide sequence is provided as set forth in SEQ ID NO:2

As used herein, the term "Mig3 polypeptide" refers to the polypeptide sequence provided in FIG. 14 as SEQ ID NO: 3. The polypeptide sequence for the Mig2 protein is provided as SEQ ID NO: 4 in FIG. 14. The polypeptide sequence for the Mig1 protein is provided in FIG. 14 as SEQ ID NO: 5. An exemplary nucleotide sequence which encodes the Mig3 protein is provided by SEQ ID NO: 6 as set forth in Genbank Accession No: NP_010945.

A "polypeptide substantially identical to the Elo1 polypeptide" varies from the Elo1 polypeptide (SEQ ID NO:1) but has at least 80%, preferably at least 85%, more preferably at least 90%, and yet more preferably at least 95% sequence identity at the amino acid level over the complete amino acid sequence, and, in addition, it possesses fatty acid elongation enzymatic activity. A "polypeptide substantially identical to the Mig3 polypeptide" varies from the Mig3 polypeptide (SEQ ID NO:3) but has at least 80%, preferably at least 85%, more preferably at least 90%, and yet more preferably at least 95% sequence identity at the amino acid level over the complete amino acid sequence.

The term "substantial sequence homology" refers to DNA or RNA sequences which have de minimus sequence variations from, and retain substantially the same biological functions as the corresponding sequences to which comparison is made. In the present invention, it is intended that sequences having substantial sequence homology to the nucleic acid encoding the Elo1 polypeptide are identified by: (1) their encoded gene product possessing fatty acid elongating enzymatic activity similar to the Elo1 polypeptide; and (2) their ability to hybridize to the sequence of SEQ ID NO: 2 under stringent conditions. In the present invention, it is intended that sequences having substantial sequence homology to the nucleic acid encoding the Mig3 polypeptide are identified by their ability to hybridize to the sequence of SEQ ID NO: 6 under stringent conditions.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11; incorporated herein by reference as if set forth in its entirety. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM NaH$_2$PO$_4$, and 1.25 mM EDTA, pH 7.4) can be substituted for SSC (1×SSPE is 0.15 M NaC and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (T$_m$) of the hybrid, where T$_m$ is determined according to the following equations. For hybrids less than 18 base pairs in length, T$_m$ (° C.)=2(# of A+T bases)+4(# of G+C bases). For hybrids between 18 and 49 base pairs in length, T$_m$ (° C.)=81.5+16.6(log$_{10}$[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M NaH$_2$PO$_4$, 7% SDS at about 65° C., followed by one or more washed at 0.02M NaH$_2$PO$_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a reporter gene operably linked to a SV40 promoter). A "heterologous gene" shall refer to a gene not naturally present in a host cell (e.g., a luciferase gene present in a retinoblastoma cell line).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The term "biofuel" refers to a wide range of fuels which are in some way derived from biomass. The term covers solid biomass, liquid fuels and various biogases. For example, bioethanol is an alcohol made by fermenting the sugar components of plant materials and it is produced largely from sugar and starch crops. Cellulosic biomass, such as trees and grasses, are also used as feedstocks for ethanol production and the present invention finds its primary application in this specific field. Of course, ethanol can be used as a fuel for vehicles in its pure form, but it is usually used as a gasoline additive to increase octane and improve vehicle emissions.

"Yeasts" are eukaryotic micro-organisms classified in the kingdom Fungi. Most reproduce asexually by budding, although a few undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is shown by their placement in separate phyla, principally the *Ascomycota* and the *Basidiomycota*. The budding yeasts ("true yeasts") are classified in the order Saccharomycetales.

II. The Invention

Ethanol production from lignocellulosic biomass holds promise as an alternative fuel. However, industrial stresses, including ethanol stress, limit microbial fermentation and thus prevent cost competitiveness with fossil fuels. To identify novel engineering targets for increased ethanol tolerance, the present inventors took advantage of natural diversity in wild *Saccharomyces cerevisiae* strains. The inventors previously showed that an S288c-derived lab strain cannot acquire higher ethanol tolerance after a mild ethanol pretreatment, which is distinct from other stresses. The inventors subsequently measured acquired ethanol tolerance in a large panel of wild strains and show that most strains can acquire higher tolerance after pretreatment. They exploited this major phenotypic difference to address the mechanism of acquired ethanol tolerance, by comparing the global gene expression response to 5% ethanol in S288c and two wild strains. Hundreds of genes showed variation in ethanol dependent gene expression across strains. Computational analysis identified several transcription factor modules and known co-regulated genes as differentially expressed, implicating genetic variation in the ethanol signaling pathway. The inventors used this information to identify genes required for acquisition of ethanol tolerance in wild strains, including new genes and processes not previously linked to ethanol tolerance, and six genes that increase ethanol tolerance when over expressed. One of these genes, Elo1, is implicated in fatty acid elongation, which prompted the inventors to compare lipidomic profiles across strains. An additional gene of interest, Mig3, which is a transcription factor that plays an obscure role in yeast cellular physiology, was investigated in terms of its ability to increase ethanol resistance in yeast. The inventors' approach shows that comparative genomics across natural isolates can be used to identify genes for industrial engineering while expanding the field's understanding of natural diversity.

In view of the inventors' discoveries, the present invention provides an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid.

The present invention will employ strong heterologous promoters, preferably inducible versions thereof. Suitable promoters for use in the invention include, e.g., the ACT1, PGK1, TDH3, TEF1, or TEF2 promoters, or promoters of other highly expressed *S. cerevisiae* genes. In preferred embodiments, the promoter is an inducible heterologous promoter and ethanol tolerance in the recombinant yeast is conferred by induction of the inducible heterologous promoter. Inducible heterologous promoters suitable for use in the present invention include, e.g., the GAL4, CUP1, PHO5, or tetO7 promoter.

In another aspect, the invention is directed to a recombinant yeast engineered to contain an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid. In an alternative aspect, the invention is directed to a recombinant yeast engineered to contain isolated nucleic acids comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; and (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acids provides increased ethanol tolerance in the recombinant yeast relative to a control yeast lacking expression of the isolated nucleic acids.

The recombinant yeast is preferably of the genus *Saccharomyces*, more preferably of the species *Saccharomyces cerevisiae*. Such recombinant yeast will have at least one copy of the gene which increases ethanol tolerance, and may have two or more, usually not exceeding about 200, depending upon whether the construct is integrated into the genome, amplified, or is present on an extrachromosomal element having multiple copy numbers. Integration or non-integration may be selected, depending upon the stability required for maintenance of the extrachromosomal element, the stability of the particular extrachromosomal element prepared, the number of copies desired, the level of transcription available depending upon copy number, and the like.

As can be appreciated, the present invention contemplates the use of recombinant yeast as described herein for use in the production of ethanol, including certain exemplary recombinant *Saccharomyces cerevisiae* strains specifically identified herein, including, e.g., BY4741/pEGH(ELO1) and BY4741/pEGH(MIG3).

The present invention further encompasses a method of providing a recombinant yeast having increased ethanol tolerance that is useful in biofuel production. Such a method includes steps of introducing into an isolated yeast an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into the cloning vector, the vector transformed into a cloning host, e.g. *E. coli*, the cloning host grown up, lysed, the plasmid isolated and the fragment analyzed by restriction analysis, sequencing, combinations thereof, or the like.

Various vectors may be employed during the course of development of the construct and transformation of host cells. Thee vectors may include cloning vectors, expression vectors, and vectors providing for integration into the host or the use of bare DNA for transformation and integration. The cloning vector will be characterized, for the most part, by having a replication original functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host. Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions. Of particular interest for the subject invention as the vector for expression, either for extrachromosomal stable maintenance or integration, are constructs and vectors which in their stable form in the host are free of prokaryotic DNA.

Figure 13:
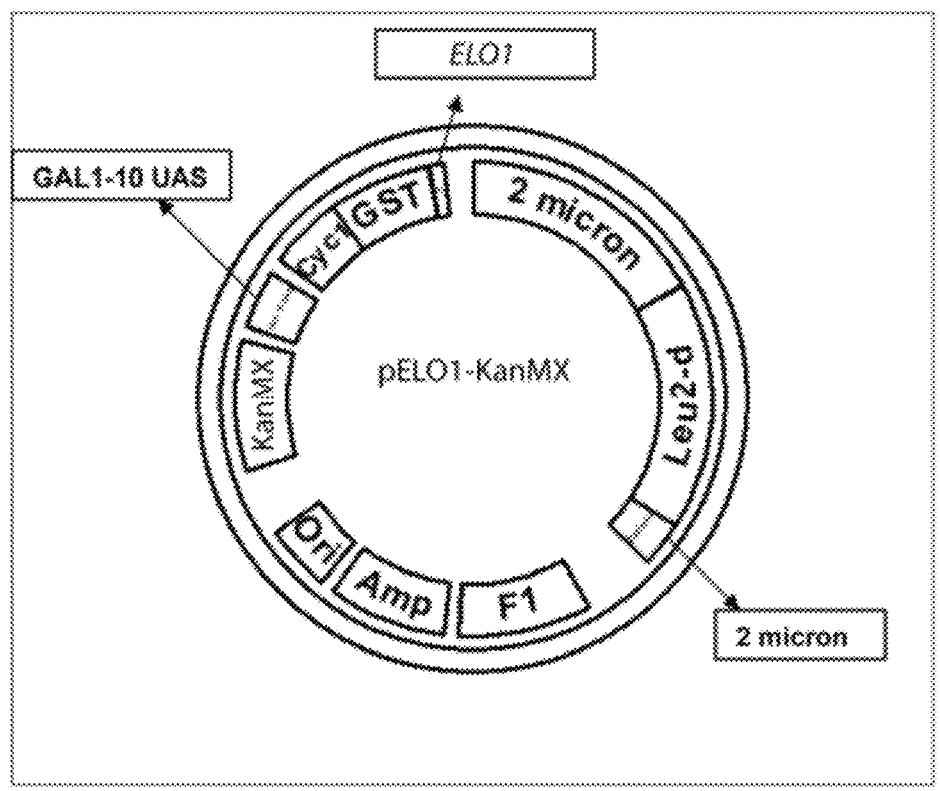
FIG. 13 depicts a map of an exemplary Elo1 over-expression vector that uses the KanMX (kanamycin resistance) marker.

For extrachromosomal stable maintenance, it may be necessary to provide for selective pressure on those hosts maintaining the construct. Stable maintenance may be achieved by providing for resistance against a cytotoxic agent, e.g. an antibiotic, such as kanamycin or G418, or by imparting prototrophy to an auxotrophic host. For stable maintenance in a yeast host, the 2 micron origin of replication may be employed or a combination of a centromere, e.g. CEN3, and ars. For integration, generally homologous integration will be desirable, so that the construct will be flanked by at least about 50 bp, more usually at least about 100 bp on each side of the construct of a sequence homologous with a sequence present in the genome of the host. FIG. 13 illustrates an exemplary Elo1 vector suitable for over-expression that uses the KanMX (kanamcyin resistance) marker.

The yeast host may be transformed in accordance with conventional ways. Conveniently, yeast protoplasts may be transformed in the presence of a fusogen, such as a non-ionic detergent, e.g. polyethyleneglycol.

Yeast strains that may serve as yeast hosts include, for example, certain yeast strains useful in biofuel production such as, e.g., BY4741, YB210, CEN.PK, PE-2, BG-1, CAT-1, SA-1, VR-1, JAY270, or 424A(LNH-ST) and derivatives thereof.

In another aspect, the present invention provides a method for producing ethanol from a recombinant yeast. Such a method includes steps of: culturing under ethanol-producing conditions a recombinant yeast engineered to contain an isolated nucleic acid comprising: (a) a nucleotide sequence encoding the Elo1 polypeptide of SEQ ID NO:1 or a polypeptide substantially identical to the Elo1 polypeptide of SEQ ID NO: 1 that is capable of enzymatic elongation of fatty acids; or (b) a nucleotide sequence encoding the Mig3 polypeptide of SEQ ID NO:3, a polypeptide substantially identical to said Mig3 polypeptide of SEQ ID NO:3, or a nucleotide sequence which hybridizes under stringent conditions to SEQ ID NO:6, or to a fully complementary nucleotide sequence of SEQ ID NO: 6, wherein expression in a recombinant yeast of said isolated nucleic acid provides increased ethanol tolerance in the recombinant yeast relative to a control yeast lacking expression of the isolated nucleic acid; and isolating ethanol produced by the recombinant yeast.

In certain embodiments, at least a portion of the culturing step takes place in a culture medium having an ethanol concentration of greater than about 15% (v/v). In yet other embodiments, at least a portion of the culturing takes place in a culture medium having an ethanol concentration of greater than about 20% (v/v).

In view of the various industrial uses and storage conditions the present recombinant yeasts will be subjected to, the invention further encompasses yeast inoculums which contain at least (a) a recombinant yeast engineered according to the present invention; and (b) a culture medium.

The following experimental data are provided to illustrate the invention. It is to be understood that a person skilled in the art who is familiar with the methods may use other yeast strains and vectors which can be equally used for the purpose of the present invention. These alterations are included in the scope of the invention.

III. Examples

Example 1

Natural Variation in Acquired Ethanol Tolerance in Diverse Yeast Strains

The inventors previously showed that an S288c-derived lab strain, pretreated with individual mild stressors, can acquire increased tolerance to either the same or different stresses. However, ethanol was the only pretreatment that did not increase resistance to subsequent stresses, including ethanol itself (FIG. 1A). This raised the question of whether ethanol was unique as a stressor, or whether the S288c laboratory strain was anomalous. To test this, the inventors performed acquired ethanol tolerance assays on 47 diverse strains from vineyards, oak exudate, sake and wine fermentations, clinical settings, and other natural environments. Cells were exposed to 5% ethanol for 60 min, then exposed to a panel of 11 high doses of ethanol (FIG. 1 and Methods). Intriguingly, most (but not all) strains tested could acquire further ethanol tolerance after mild pretreatment (FIG. 1B). The major progenitor strain of S288c, EM93, showed some acquisition of ethanol tolerance after a pretreatment (FIG. 1B), suggesting S288c lost this ability relatively recently. The inventors subsequently focused on two wild strains—oak-soil strain YPS163 and the vineyard strain M22—to probe the physiology of acquired ethanol resistance.

Example 2

Variation in the Genomic Expression Response to Ethanol

Figure 2:
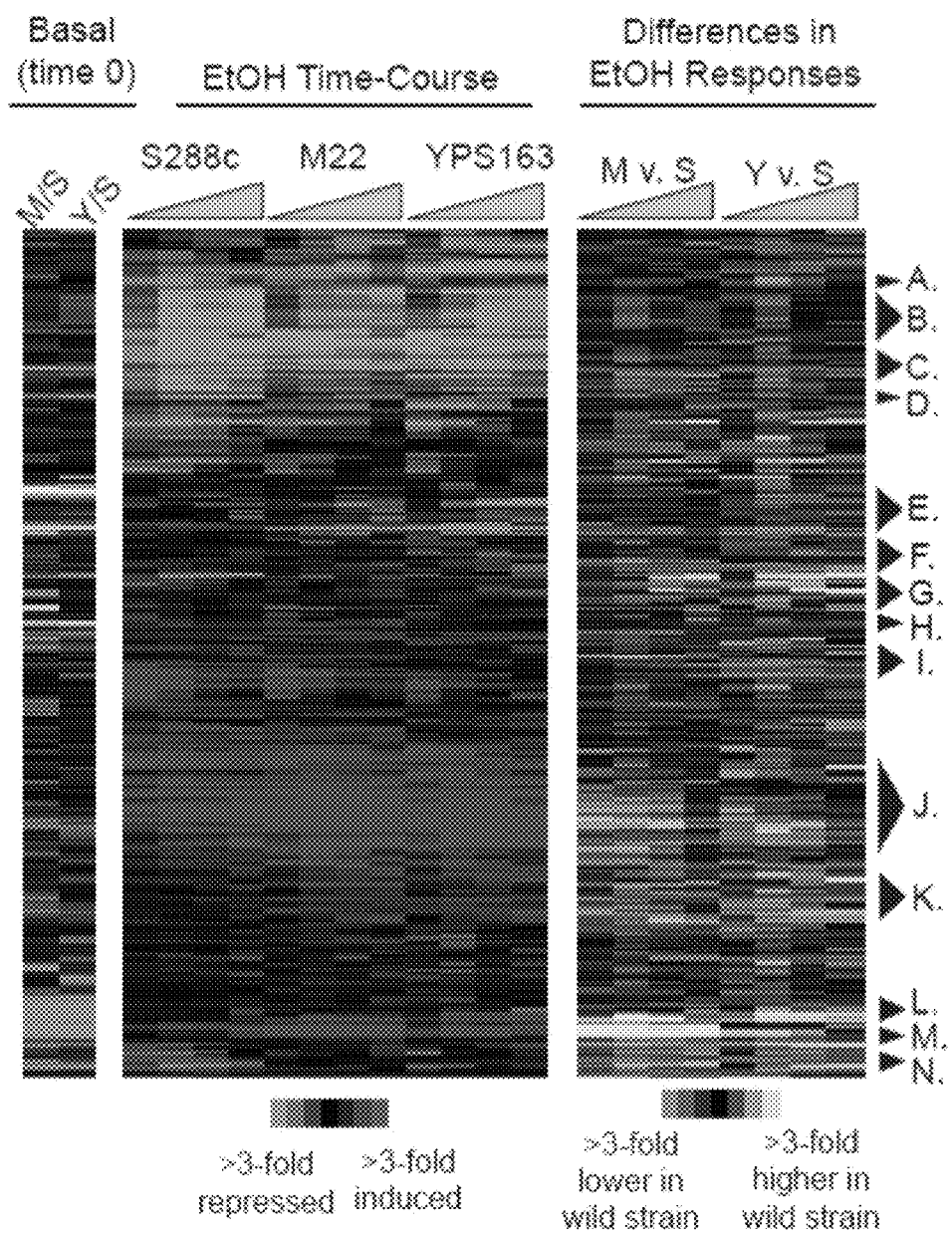
FIG. 2 depicts the variation in gene expression between S288c, M22, and YPS163. Log 2 ethanol-responsive expression changes of 2203 genes differentially expressed in either wild strain versus S288c (FDR=0.05, paired t-test). Basal expression differences in M22 (M) or YPS163 (Y) versus S288c (S) are shown on the left; time-courses of the expression changes in response to ethanol are shown in the middle; and difference between ethanol response in each wild strain versus S288c is shown on the right. Each row represents a gene and each column represents a strain or condition, with time-course samples indicated by triangles. Genes were organized by hierarchical clustering of the combined basal expression and time-course data. Differences in ethanol response across strains were subsequently added to the figure. Red indicates induced and green indicates repressed expression in response to ethanol. Blue indicates higher and yellow indicates lower expression in S288c relative to the wild strains.
Figure 6:
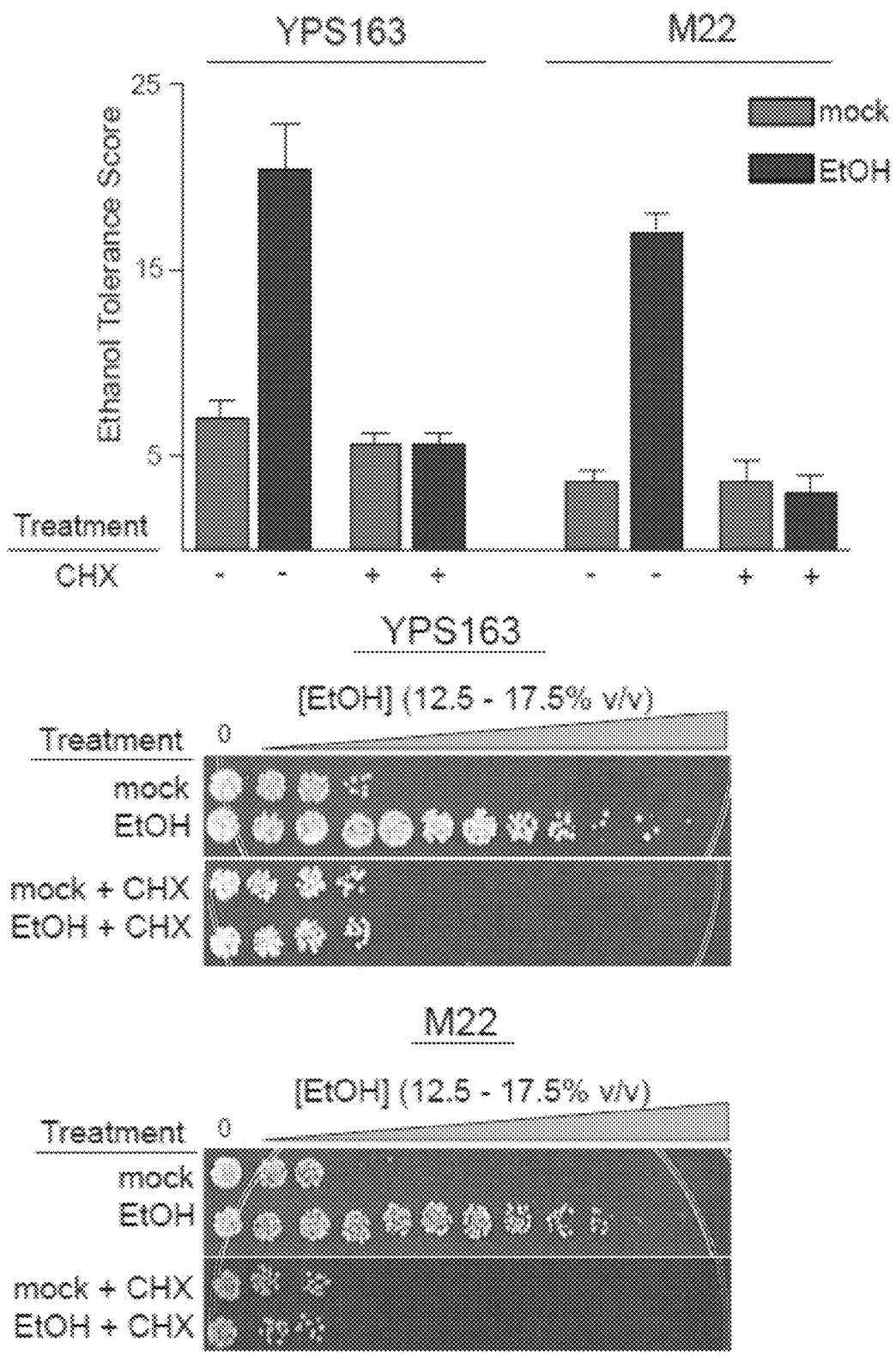
FIG. 6 depicts cycloheximide blocks acquired ethanol tolerance in both YPS163 and M22. The middle panels depict results of a spot assay for acquired ethanol tolerance as performed in FIG. 1A. Error bars represent standard deviation of biological triplicates. The lower panel represents a representative spot assay from the experiment. Cycloheximide (CHX), if present, was added 20-min prior to either the mock or ethanol (5%) primary stress.
Figure 7:
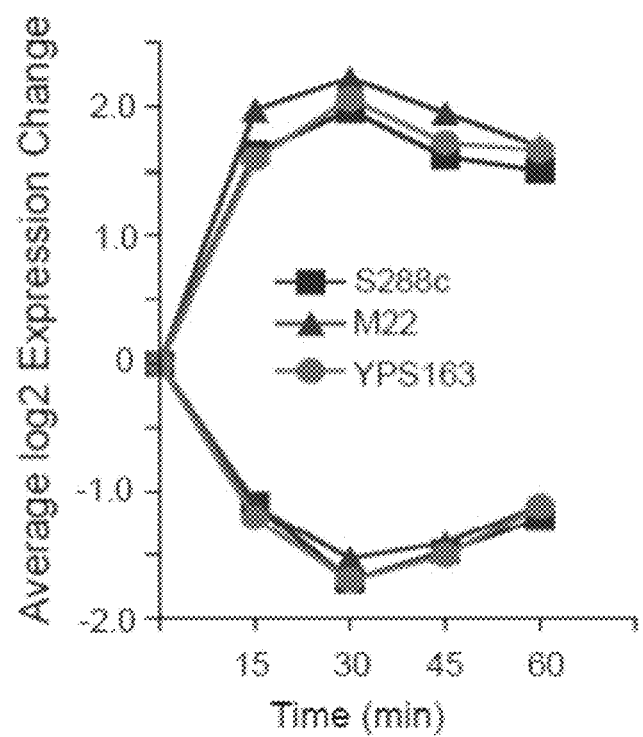
FIG. 7 depicts gene expression kinetics of the ethanol response in S288c, M22, and YPS163. The average log 2 expression ratio for each time point was calculated using only the genes that were induced or repressed by >2-fold.

Acquired resistance to several stresses requires nascent protein synthesis during the mild-stress pretreatment. Consistently, the inventors found that acquired ethanol resistance in wild strains also requires protein synthesis during pretreatment (FIG. 6). They therefore suspected that S288c may have an altered genomic expression response to ethanol. They used whole-genome DNA microarrays to measure the gene expression response of S288, YPS163, and M22 responding to 5% ethanol over a 60 minute time course (FIG. 2). To identify statistically significant differences between strains, the inventors performed biological triplicates before and at 30 min after ethanol treatment, which encompassed the peak response. As expected, ethanol induced a dramatic remodeling of the yeast transcriptome. Over half of the genome (3941 genes, False discovery rate, FDR=0.01) was significantly affected by ethanol in any of the three strains, with similar kinetics (FIG. 7). Genes induced >3-fold were enriched for certain functional categories, including vacuolar catabolic processes, response to temperature stimulus, glucose metabolism, alcohol catabolism and metabolism of energy reserves including glycogen and trehalose (Bonferroni-corrected p<0.01 in all cases). The genes significantly repressed >3-fold by ethanol were strongly enriched for ribosome biogenesis and protein synthesis.

Together, these results are consistent with activation of the yeast environmental stress response, and largely agree with the previous literature. The inventors next identified genes with larger ethanol-responsive induction in wild strains compared to S288c, reasoning that they may account for the phenotypic difference in acquired ethanol tolerance. They therefore identified expression differences between each wild strain compared directly to S288c (FDR<0.05). There were 1555 genes (25%) and 1662 genes (27%) differentially expressed in response to ethanol in M22 and YPS163, respectively, compared to S288c-875 of these genes were common to both comparisons. In contrast, the two wild strains compared to each other showed differential ethanol response at only 735 genes, revealing a large fraction of S288c-specific differences. A fraction (38-45%) of the 875 ethanol-responsive genes that distinguish S288c from the wild strains also showed underlying differences in basal gene expression (393/875 in M22 compared to S288c and 329/875 in YPS163 versus S288c). However, there was little overlap in functional groups enriched in genes with basal expression differences compared to genes with variation in ethanol response. Together, this indicates significant variation in the gene expression response to ethanol.

Example 3

Figure 3:
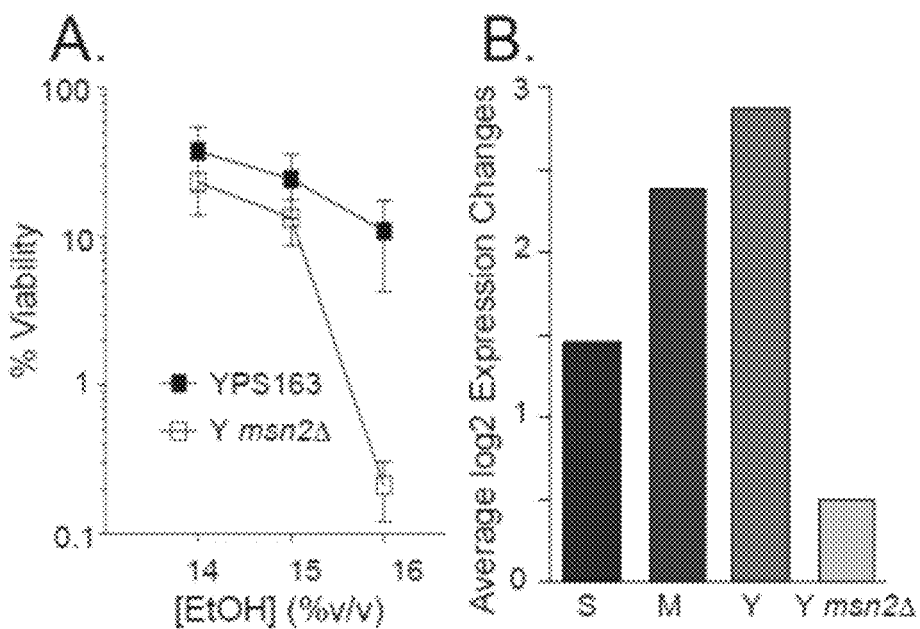
FIG. 3 shows that acquired ethanol tolerance depends on Msn2. A) Acquired tolerance defect of an msn2Δ strain. Cells were pre-treated with 5% (v/v) ethanol for 1 h and then subjected to severe ethanol doses (x-axis) for 2 h. Colony-forming units indicated % viability. Error bars represent standard deviation of biological triplicates. B) Average log 2 expression change of 106 Msn2-dependent genes with significantly lower expression in S288c versus YPS163, in S288c (S), M22 (M), YPS163 (Y), and YPS163 (Y) msn2Δ strains responding to ethanol.
Figure 4:
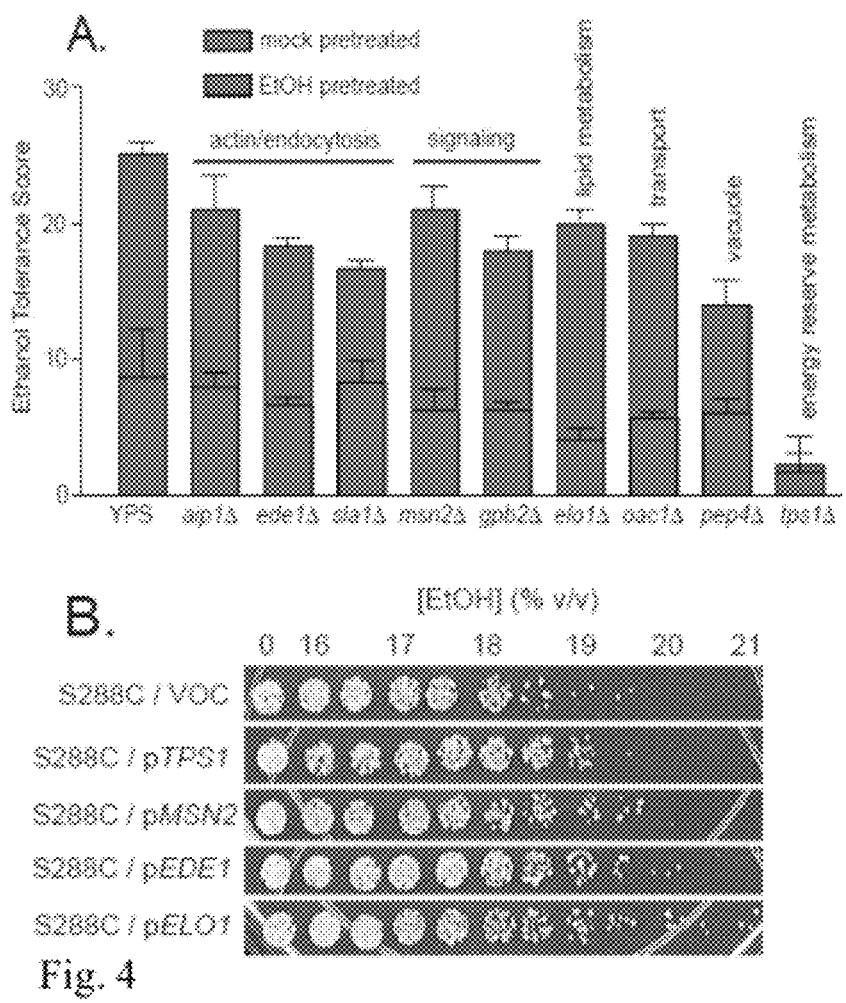
FIG. 4 depicts genes necessary for acquired ethanol resistance. A) Basal and acquired ethanol tolerance is shown for various mutant strains. The average and standard deviation of ethanol tolerance scores (see Methods) is shown for strains pretreated with 5% ethanol (blue) versus the mock-treated control (orange). Error bars represent standard deviation of biological triplicates. B) A representative experiment showing strain tolerances to 2 h exposure of indicated ethanol doses in S288c containing the indicated galactose-inducible plasmid constructs (see Methods). Data are as shown in FIG. 1A.
Figure 8:
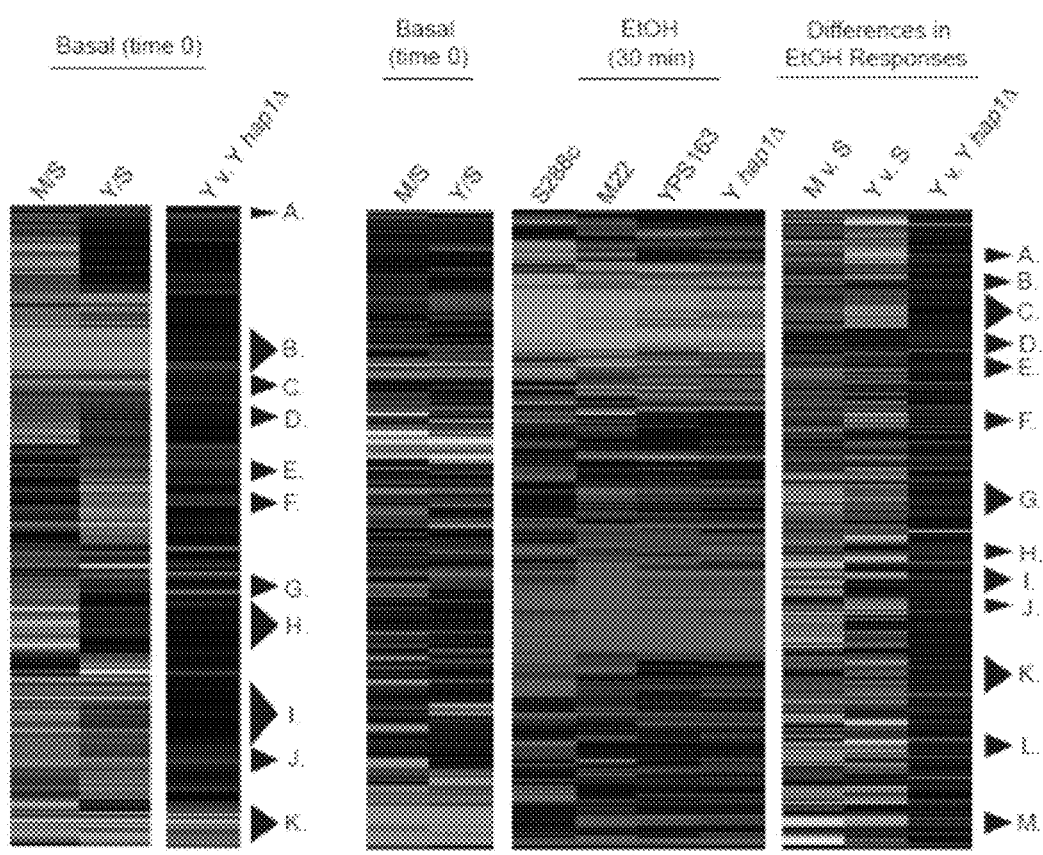
FIG. 8 depicts the hierarchical clustering of gene expression differences in a YPS163 hap1Δ strain. The diagrams show the average log 2 expression differences in the denoted strains, as shown in FIG. 2. Genes were organized independently for panels shown on the left and on the right by hierarchical clustering. A red color indicates genes induced by ethanol and a green color indicates genes repressed by ethanol. A blue color indicates genes with higher expression in S288c or the hap1Δ strain relative to YPS163, and a yellow color indicates higher expression in the YPS163 relative to S288c or the hap1Δ strain. The left panel denotes 2304 genes with either basal gene expression differences in either wild strain compared to S288c (FDR=0.05, t-test) or significant differences in gene expression in the YPS163 hap1Δ strain compared to YPS163 (FDR=0.05, paired t-test). The results show that deletion of hap1 only accounts for a small fraction of basal gene expression differences between wild strains and S288c, the latter of which contains a known polymorphism that reduces Hap1 function. The right panel denotes 2590 genes with either differences in ethanol-induced gene expression in either wild strain versus S288c (FDR=0.05, paired t-test), or significant differences in gene expression in the YPS163 hap1Δ strain compared to YPS163 (FDR=0.05, paired t-test). Again, Hap1 accounts for a small number of ethanol-dependent gene expression differences between the wild strains and S288c.
Figure 9:
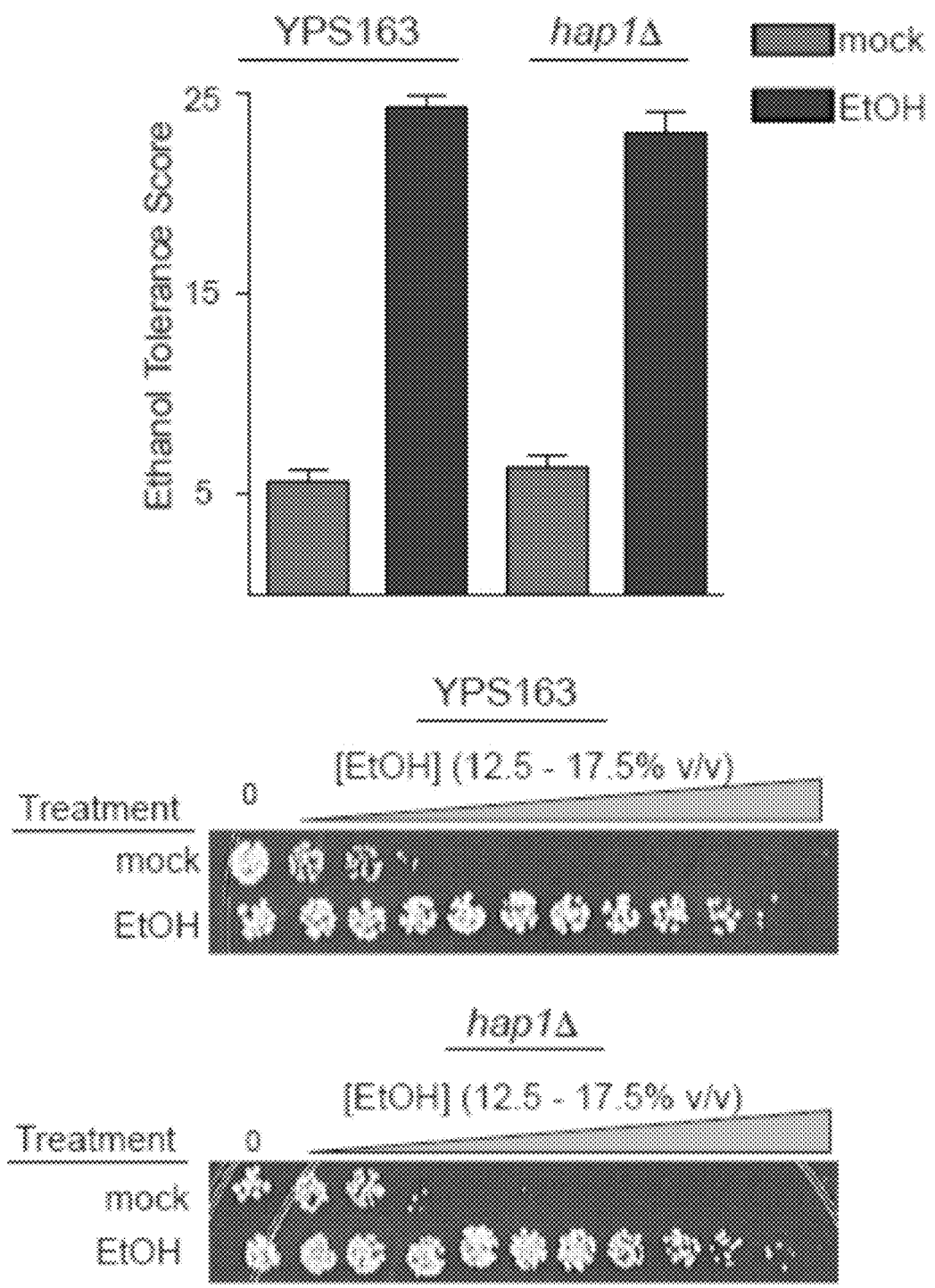
FIG. 9 depicts that Hap1 is not required for acquired ethanol tolerance. The middle panel depicts results of a spot assay for acquired ethanol tolerance as described in FIG. 1A and Methods. Error bars represent standard deviation of biological triplicates. The lower panel shows a representative spot assay from the experiment.
Figure 10:
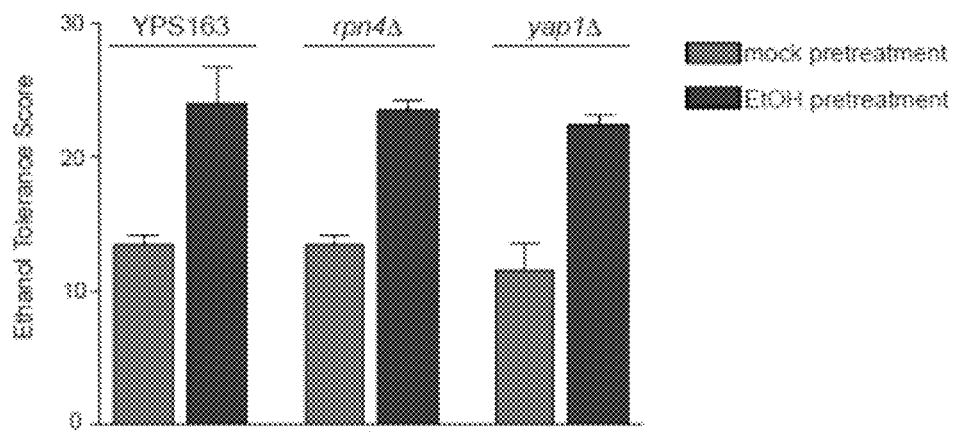
FIG. 10 depicts Rpn4 and Yap1 are not required for acquired ethanol tolerance. Results of a spot assay for acquired ethanol tolerance as described in FIG. 1A and Methods. Error bars represent standard deviation of biological duplicates.
Figure 11:
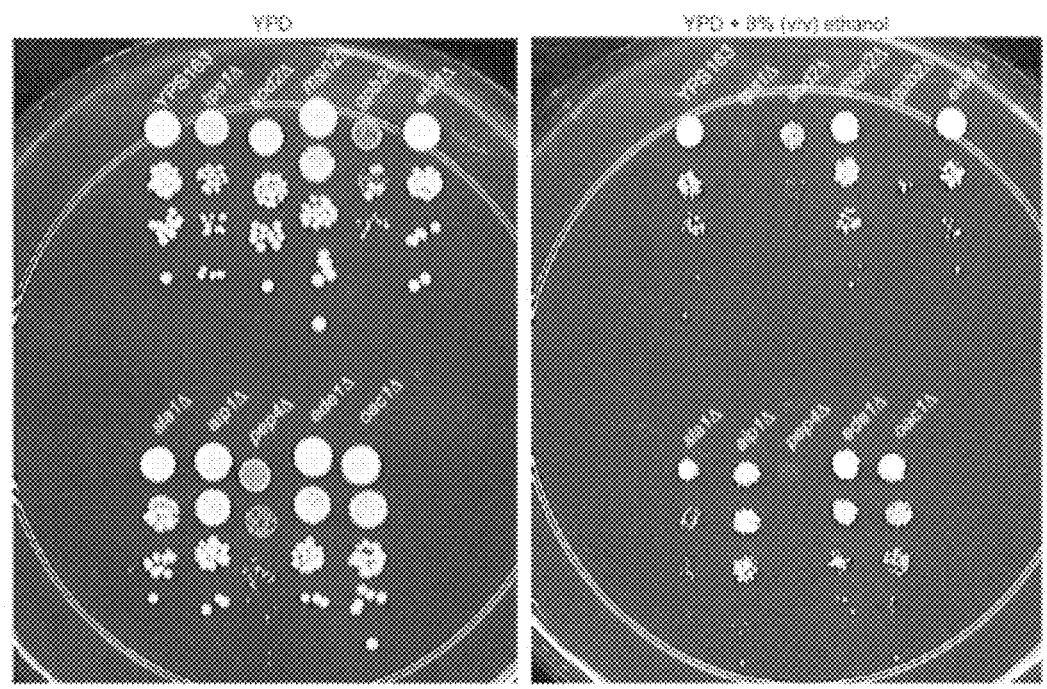
FIG. 11 depicts the growth analysis of mutants with defects in acquired ethanol resistance on YPDE plates. Cells were grown at least 8 generations to an OD600 of 0.3-0.6, after which cells were normalized to an OD600 of 0.15 and 10-fold serial dilutions were plated onto either a YPD (control) plate or YPD+8% (v/v) ethanol. Growth on the YPD plate was scored at 2 days, while growth on the YPDE plate was scored at 3 days.

Network Analysis Implicates Transcription Factors Underlying Expression Differences To identify patterns in the dataset, the inventors hierarchical clustered ~2300 genes with ethanol-dependent expression differences in either strain compared to S288c (FDR<0.05, FIG. 2). They systematically scored enrichment of GO functional categories for each cluster. Several gene clusters with higher induction in both wild strains were enriched for functional categories, including vacuolar protein catabolism, trehalose biosynthesis, response to oxidative stress, alcohol metabolism, and proteolysis (Cluster J), and transposition (Clusters L and M). Several gene clusters actually showed higher induction in S288c, such as oxidative phosphorylation and cellular respiration (Cluster H) and protein folding (Cluster I). These may represent processes that are more strongly affected by ethanol in the S288c background. The results of the clustering analysis suggested upstream differences in physiology and/or ethanol signaling that affected many genes in trans. The inventors sought to implicate transcription factors required for a robust ethanol response, and to examine whether variability in transcription factor function was responsible for S288c's inability to mount a proper response to ethanol. They first ruled out a known polymorphism in the S288C HAP1 gene, which encodes a transcription factor involved in heme and oxygen sensing (FIGS. 8, 9). Clustering analysis and transcription factor-target enrichment implicated three additional transcriptional regulators: Rpn4, which regulates proteasome genes, the oxidative-stress transcription factor Yap1, and the stress-activated factor Msn2. The targets of Rpn4 and Yap1 showed weaker induction in S288c compared to both wild strains, indicating variation in their responsiveness to ethanol. However, neither Rpn4 nor Yap1 had an effect on acquired ethanol tolerance, as mutants lacking either gene acquired ethanol resistance at wild-type levels (FIG. 10). In contrast, deletion of msn2 in YPS163 impaired both acquired ethanol resistance and gene expression. The YPS163 msn2Δ mutant showed reduced acquisition of ethanol tolerance after pretreatment but no difference in basal ethanol tolerance (FIGS. 3A, 4A). Transcriptional profiling of the YPS163 msn2Δ mutant responding to 5% ethanol identified 244 genes with attenuated gene induction (FDR<0.01, Dataset S3), confirming involvement of Msn2 in the ethanol response. One-hundred and six of the 239 Msn2-regulated genes (44%, $p=4\times10^{-9}$, Fisher's exact test) also had significantly lower induction in S288c responding to ethanol compared to YPS163 (FIG. 3B). This suggests the Msn2 activation by ethanol is partially defective in S288c, and implicates one or more Msn2 targets as likely direct effectors of acquired ethanol tolerance.

Example 4

Identifying Mutants with Defects in Acquired Ethanol Resistance

To identify additional effectors of acquired ethanol resistance, the inventors generated deletion mutants of 20 manually chosen genes, implicated by their reduced induction in S288c (see Methods). Strikingly, over 50% of the genes interrogated were required for normal acquisition of ethanol tolerance, indicating that our method strongly enriched for required genes. The inventors identified eight genes (in addition to MSN2) that were necessary for acquired ethanol resistance (ELO1, SLA1, AIP1, TPS1, EDE1, GPB2, PEP4, and OAC1; FIG. 4A).

Example 5

Strain Specific Differences in Lipid Composition

Figure 5:
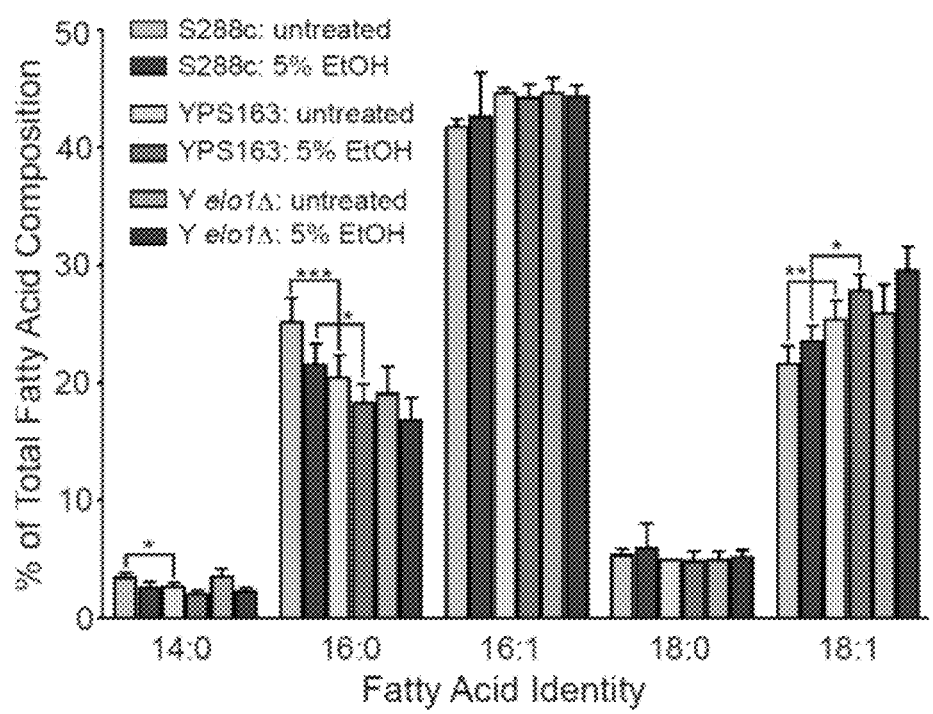
FIG. 5 depicts the differences in membrane lipid composition in response to ethanol in S288c and YPS163. GC-MS analysis of the total membrane lipids in response to ethanol in S288c, YPS163, or the YPS163 (Y) elo1Δ mutant. The x-axis represents lipid chain length and level of saturation. Error bars represent standard error of biological triplicates. Asterisks denote significantly different comparisons between YPS163 and S288c (*=p<0.05, =p<0.01, *=p<0.001, paired t-test).

The requirement for fatty acid Elongase I (Elo1) raised the possibility that S288c may not properly remodel its plasma membrane in response to the fluidizing effects of ethanol. The inventors therefore performed gas chromatography mass spectrometry (GC-MS) analysis of the total membrane fatty acids from S288c, YPS163, and the YPS163 elo1Δ strain, either in the presence or absence of 5% ethanol. In response to ethanol, YPS163 increased the proportion of oleic acid (18:1) in the membrane, with a commensurate decrease in palmitic acid (16:0) (FIG. 5). Indeed, higher levels of oleic acid are known to correlate with higher ethanol tolerance. The membrane lipid profile of S288c contrasted with YPS163, since basal levels of palmitic acid were higher while oleic acid was lower in S288c. Upon ethanol treatment, S288c was able to increase its oleic acid content but not to levels seen in YPS163 (FIG. 5). Thus, the difference in lipid content in S288c correlates with its inability to acquire ethanol resistance after a mild pretreatment. Given that the YPS163 strain lacking ELO1 had a defect in acquired ethanol tolerance, the inventors expected it would have lower levels of long-chain fatty acids, and specifically oleic acid (C18:1). Starting levels of 14:0 were slightly higher than the YPS163 parent, similar to the S288c strain (FIG. 5). However, following ethanol treatment the membrane lipid profile of the YPS163 elo1Δ strain did not differ measurably from wild-type YPS163. The effect of Elo1 on lipid profiles may be obscured by technical limitations of the study, since the inventors were unable to observe subclasses of these lipids.

Example 6

Viability of Over-Expression Strains

Figure 12:
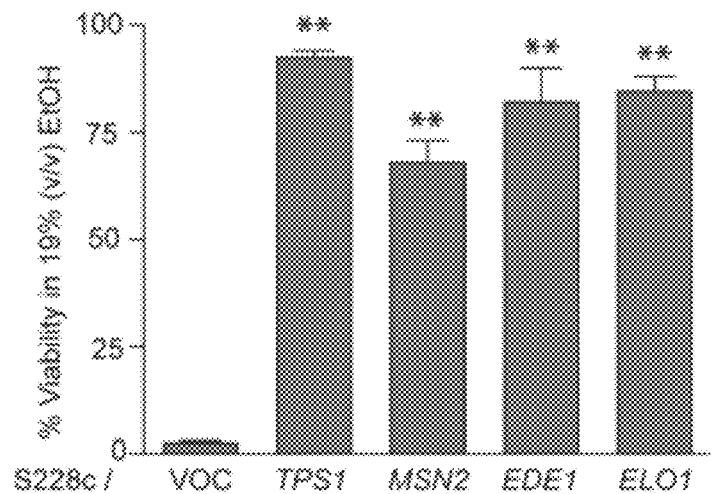
FIG. 12 depicts viability of over-expression strains scored for a 2 hour exposure to 19% ethanol.

Referring to FIG. 12, viability of over-expression strains was scored for a 2 h exposure to 19% ethanol using flow cytometry to determine the proportion of propidium iodide negative (i.e. live) cells. Error bars represent standard deviation of biological triplicates. Asterisks denote significant differences in % viability relative to S288c carrying the vector only control (**=$p<0.01$, t-test).

Example 7

Materials and Methods: Strains, Culture Media, and Growth Conditions Uses in Examples 1-6

All chemicals were purchased from Sigma (St. Louis, Mo.). Gene deletions were created by homologous recombination that replaced the gene coding sequence with KanMX3 drug resistance cassettes. The HO gene was replaced with the HygMX3 cassette to generate a haploid YPS163 upon dissection, and this was used as the background in all YPS163 strain knockouts. The haploid strain behaved similarly to the diploid strain in all ethanol resistance assays (compare FIGS. 6 (diploid) and 9 (haploid)). All mutations were confirmed by diagnostic PCR.

Ethanol resistance assays. Acquired ethanol resistance was assayed as in (Berry, D. B., Gasch, A. P. (2008) Stress-activated genomic expression changes serve a preparative role for impending stress in yeast. *Mol Biol Cell* 19:4580-4587, incorporated herein by reference as if set forth in its entirety). Briefly, cultures were grown in YPD (1% yeast extract, 2% peptone, 2% glucose) for at least 8 generations to an optical density (OD600) of 0.3. Each culture was split into two cultures and received either a single dose of 5% (v/v) ethanol or 5% water as a mock control. Mock-treated cells were thereafter handled identically. Cells were exposed to a panel of severe ethanol doses (ranging from 5-25% v/v depending on the experiment) in YPD for 2 h in 96-well plates. A 50-fold dilution of each culture was spotted onto YPD agar plates and grown for 48 h, after which viability at each dose was scored by visual inspection using a four-point scale to score 100%, 50-100%, 10-50%, or 0% survival compared with the no stress (YPD) control. An overall ethanol tolerance score was calculated as the sum of scores over 11 doses of stress. Cycloheximide experiments were performed as above, except that 10 μg/ml cycloheximide was added to the culture 20 min before and throughout the ethanol pretreatment. A mock-treated culture received inhibitor treatment but no primary stress. Long-term ethanol tolerance was scored by plating cells on YPD+8% (v/v) ethanol. Growth was scored after 3 days (or 2 days in the case of controls). To measure the effects of gene over-expression, BY4741 cells harboring galactose-inducible, GST-tagged constructs (Open Biosystems, Huntsville, Ala., were grown overnight on SC-Ura containing 2% dextrose, and then subcultured for at least 8 generations in SC-Ura containing 2% galactose to induce over-expression before exposure to ethanol as described above. All overexpression strains were compared to the isogenic BY4741 containing the vector only control (pEGH). Ethanol tolerance was scored using both the spot assay described above and flow cytometry. For flow cytometry, viability was assayed using the LIVE/DEAD® FungaLight™ Yeast Viability Kit (Invitrogen, Carlsbad, Calif.) on a Guava EasyCyte flow cytometer (Millipore, Billerica, Mass.) according to both manufacturers' instructions. Briefly, mock and ethanol-treated cells were diluted 10-fold into 10 mM HEPES-NaOH (pH 7.2 at 25° C.) supplemented with 2% dextrose and the viability dye reagents (SYTO® 9 and propidium iodide). The proportion of prodium iodide negative cells was reported as percent viable cells.

Array hybridization and analysis: Cells were grown overnight for at least 8 generations to an OD600 of 0.3-0.6. A sample of cells was collected (time 0), and ethanol was added to a final concentration of 5% (v/v). Cells were collected at 15, 30, 45, and 60 min postethanol addition. A single biological replicate was collected for each strain during the timecourse. For detailed analysis of the 30-min time-point, biological triplicates were collected using a paired experimental design. Cell collection, RNA isolation, and microarray labeling were performed as described, using cyanine dyes (Flownamics, Madison, Wis.), Superscript III (Invitrogen, Carlsbad, Calif.), and amino-allyl-dUTP (Ambion, Austin, Tex.). Microarrays were spotted in house using 70 mer oligonucleotides representing each of the yeast ORFs (Qiagen, Chatsworth, Calif.). The inventors previously showed that <5% of measured expression differences could be affected by hybridization defects due to polymorphism (18). Arrays were scanned using a scanning laser (GenePix 4000B) from Molecular Devices (Sunnyvale, Calif.). Inverse dye-labeling was used in replicates to control for dye-specific effects. Data were filtered (retaining unflagged spots with $R2>0.1$) and normalized by regional mean-centering. Genes with significant expression differences in response to ethanol were identified separately for each strain by performing a t-test using the BioConductor package Limma v. 2.9.8 and FDR correction (see Dataset S3 for the Limma output). Expression differences in YPS163 or M22 relative to S288c, both with and without ethanol treatment, were identified in a similar manner. Gene clustering was done in Cluster 3.0 (bonsai.ims/utokyo.ac.jp/~mdehoon/software) using hierarchical clustering and uncentered Pearson correlation as the metric. Arrays were weighted using a cutoff value of 0.4 and an exponent value of 1. Enrichment of Gene Ontology (GO) functional categories was performed using GO-TermFinder (http://go.princeton.edu/cgibin/GOTermFinder) hosted by the Lewis-Sigler Institute for Integrative Genomics, with Bonferroni-corrected p values<0.01 taken as significant. All microarray data are available through the NIH Gene Expression Omnibus (GEO) database under accession number GSE22904.

Lipidomic GC-MS: Cells were grown in synthetic complete (SC) medium for at least 8 generations to an OD600 of 0.3-0.6. Acquired ethanol tolerance was similar in SC versus YPD (Dataset S1). Two technical replicate samples were collected for each biological sample; biological triplicates were collected. Cells were collected immediately prior to the addition of 5% (v/v) ethanol (time 0) and at 60-min after the ethanol addition. For the collections, 2-ml of cells were added directly to 200 µl concentrated HCl (final concentration of 1.1 M) and heated to 95° C. for 1 h. Total lipids were then extracted by the method of Preparation of fatty acid methyl esters (FAMEs) was performed using the method of FAMEs were analyzed by GC-MS using a Pegasus 4D GCxGC-TOF gas chromatograph-mass spectrometer (Leco Corp. St. Joseph, Mich.) fitted with a Rx1-5MS column (30 m, 0.25 mm I.D., 0.25 u df, Restek, Inc., Bellefonte, Pa.). Instrument parameters were: He carrier gas flow rate: 1 ml/min; split ratio: 5:1; injector temperature: 250° C., GC oven: 50° C. for 1 min initially, increased at 20° C./min to 330° C., and held at 330° C. for 5 minutes.

Example 8

Overexpression of Mig3 Increases Ethanol Resistance in Yeast

The Mig3 transcription factor plays an obscure role in *Saccharomyces cerevisiae* cellular physiology. Mig3 shares sequence similarity with two other transcription factors, Mig1 and Mig2 (FIG. 14). Mig1 and Mig2 are known to repress the expression of certain genes when glucose is present. However, despite homology to Mig1 and Mig2, Mig3 appears uninvolved in glucose repression. This observation was particularly surprising, since Mig3 binds to the same DNA binding motif as Mig1 and Mig2.

Gene expression studies aimed at identifying targets of Mig3 regulation have not resolved the question. Only one gene, SIR2, was significantly affected by the absence of Mig3. In contrast to the mig3Δ mutant, the mig1Δ and mig2 mutants had severe and partially overlapping defects in glucose repression.

The inventors' interest in Mig3 evolved out of studies of the ethanol response in yeast described above (see Examples 1-3). One of the genes with significantly higher induction by ethanol in the wild strains compared to S288c was MIG3. The inventors found that a wild strain harboring a mig3 deletion was defective in acquired ethanol resistance, and moreover, they found that over-expression of MIG3 dramatically increases ethanol resistance in S288c. Additionally, over-expression of MIG3 affected the expression of a number of genes, greatly expanding the number of Mig3 targets. Lastly, the inventors recapitulated previous results that found that an S288c mig3Δ strain had very few gene expression changes, but conversely in the wild strain background YPS163, a mig3Δ strain affected hundreds of genes. This demonstrates the power of using diverse strain backgrounds to identify functions for previously uncharacterized genes.

Materials and Methods

Ethanol resistance assays. All data shown are for strains in the BY4741 background (MATa his3Δ1 leu2Δ0 met15Δ ura3Δ). The msn2Δ and hsp12Δ strains were obtained from the Yeast Deletion Library (Open Biosystems). Ethanol resistance was assayed as in Berry and Gasch (2008). Briefly, cultures were grown in YPD (1% yeast extract, 2% peptone, 2% glucose) for at least 8 generations to an optical density ($OD_{600}$) of 0.3. Cells were then exposed to a panel of severe ethanol doses (ranging from 5-25% v/v depending on the experiment) in YPD for 2 h in 96-well plates. A 50-fold dilution of each culture was spotted onto YPD agar plates and grown for 48 h, after which viability at each dose was scored by visual inspection using a four-point scale to score 100%, 50-100%, 10-50%, or 0% survival compared with the no stress (YPD) control. An overall ethanol tolerance score was calculated as the sum of scores over 11 doses of stress.

Figure 16:
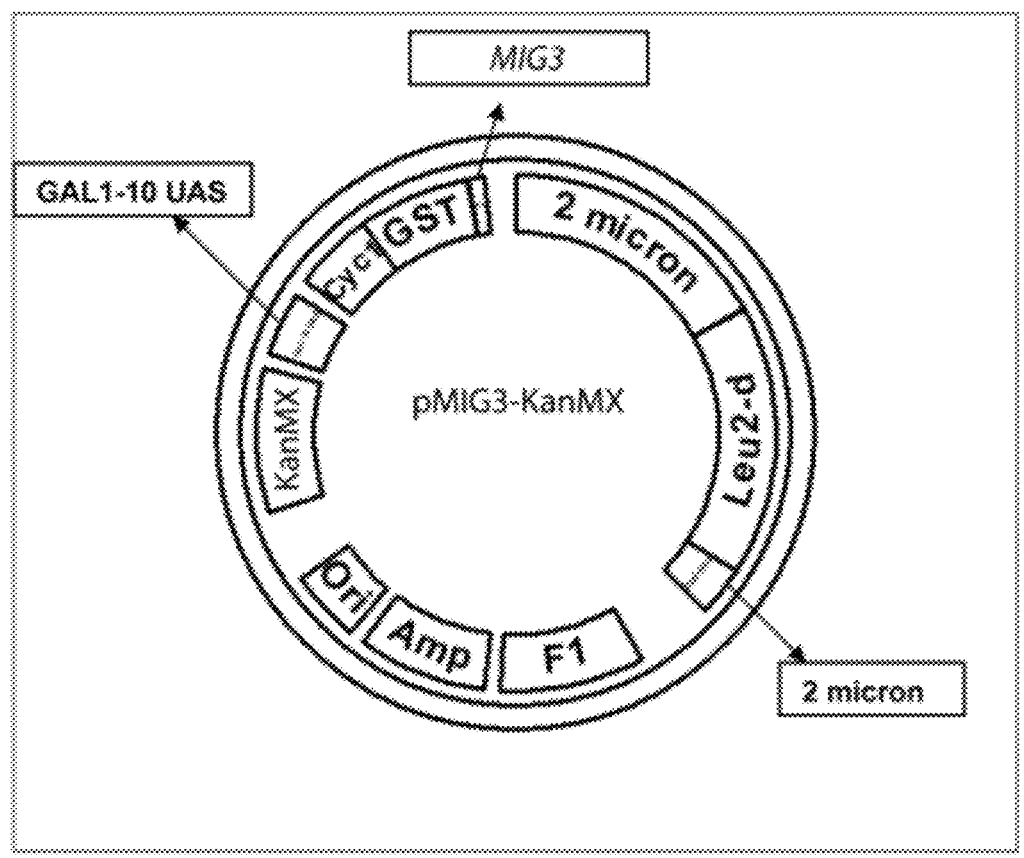
FIG. 16 depicts a schematic map of galactose-inducible, GST-tagged Mig3 construct (Mitchell, D. A., T. K. Marshall, and R. J. Deschenes 1993. Vectors for the inducible overexpression of glutathione S-transferase fusion proteins in yeast. Yeast 9:715-722, incorporated herein by reference as if set forth in its entirety).

To measure the effects of gene over-expression, BY4741 cells harboring galactose-inducible, GST-tagged constructs (Open Biosystems, Huntsville, Ala., 10 and 13; FIG. 16) were grown overnight on SC-Ura containing 2% dextrose, and then subcultured for at least 8 generations in SC-Ura containing 2% galactose to induce over-expression before exposure to ethanol as described above. All over-expression strains were compared to the isogenic BY4741 containing the vector only control (pEGH). Ethanol tolerance was scored using both the spot assay described above and flow cytometry. For flow cytometry, viability was assayed using the LIVE/DEAD® FungaLight™ Yeast Viability Kit (Invitrogen, Carlsbad, Calif.) on a Guava EasyCyte flow cytometer (Millipore, Billerica, Mass.) according to both manufacturers' instructions. Briefly, mock and ethanol-treated cells were diluted 10-fold into 10 mM HEPES-NaOH (pH 7.2 at 25° C.) supplemented with 2% dextrose and the viability dye reagents (SYTO® 9 and propidium iodide). The proportion of prodium iodide negative cells was reported as percent viable cells.

Figure 15:
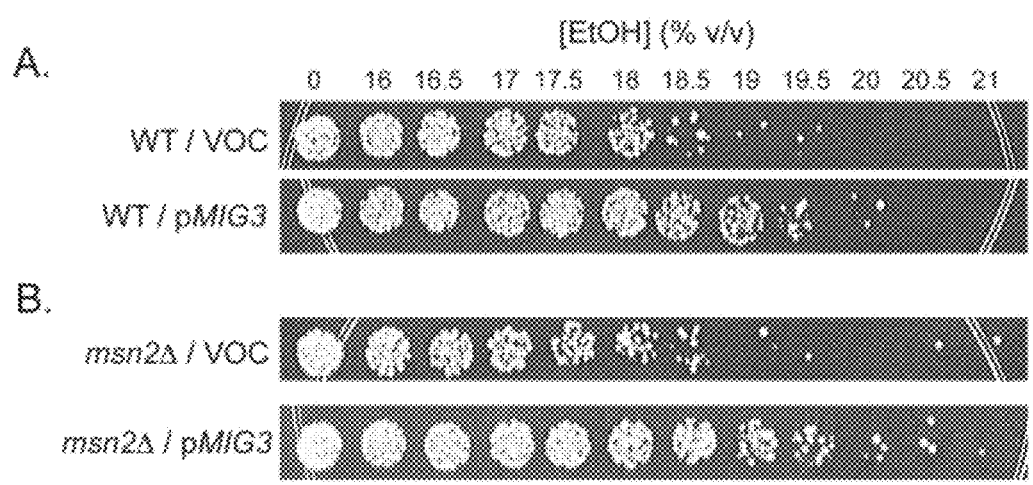
FIG. 15 depicts data showing that over-expression of Mig3 confers ethanol tolerance. A) A representative experiment showing strain basal tolerances to 2 hr exposure of indicated ethanol doses in BY4741 containing galactose-inducible Mig3 plasmid or a control vector (pEGH). B) Ethanol tolerance of a BY4741 msn2Δ mutant containing either the Mig3 over-expression vector or a control vector (pEGH).

Array hybridization and analysis. Cells harboring either GST-tagged MIG3 or the vector only control (pEGH) were grown overnight for at least 8 generations to an $OD_{600}$ of 0.3-0.6 in SC-Ura containing 2% galactose. For mig3Δ studies (in either a BY4741 or YPS163 background), cells were grown in YPD for 3 generations to an $OD_{600}$ of 0.3-0.6. A sample of cells was collected (time 0), and ethanol was added to a final concentration of 5% (v/v). All experiments were performed using biological triplicates. Cell collection, RNA isolation, and microarray labeling were performed as described (Gasch, A. P. 2002. Yeast genomic expression studies using DNA microarrays. Methods Enzymol 350:393-414, incorporated herein by reference as if set forth in its entirety), except that total RNA was labeled with a 1.7:1 molar ratio of oligo-dT and random hexamer. RNA was labeled using cyanine dyes (Flownamics, Madison, Wis.), Superscript III (Invitrogen, Carlsbad, Calif.), and amino-allyl-dUTP (Ambion, Austin, Tex.). Inverse dye-labeling was used in replicates to control for dye-specific effects. Samples were hybridized to custom Nimblegen tiled arrays and incubated on a Maui Hybridization Chamber at 42° C. for 16 h. Arrays were scanned using a scanning laser (GenePix 4000B) from Molecular Devices (Sunnyvale, Calif.), and signal from both channels was extracted following local background subtraction using the program NimbleScan. Data normalization and statistical analyses were performed using Bioconductor (Gentlemen 2004) and custom perl scripts. The affy( ) package was used to apply probe level quantile normalization. Probes with known polymorphisms in YPS163 were removed from the analysis. The $\log_2$ ratio was calculated for each gene from the median intensity of gene probes at each time point compared with that of the unstressed cells. Relative basal transcript abundance in wild-type and mig3Δ cells was performed by extracting the signal intensity corresponding to the unstressed samples and comparing across arrays Results and Discussion Using a galactose-inducible promoter, MIG3 was overexpressed in an S288c background, and found markedly increased ethanol tolerance when the strain was compared to the isogenic control strain containing the vector alone (FIG. 15A). The Mig3 protein is known to be phosphorylated and degraded in the presence of galactose, so this experiment may actually understate the effects of Mig3 over-expression on ethanol tolerance and gene expression.

The inventors previously showed that acquired ethanol resistance requires the activity of the general stress responsive transcription factor Msn2. Furthermore, over-expression of Msn2 in S288c increased the strain's ethanol resistance. The inventors tested whether Mig3 over-expression increases ethanol resistance via an Msn2-dependent mechanism. To do this, Mig3 was over-expressed in a msn2Δ strain, and assayed ethanol resistance. Over-expression of Mig3 led to the same level of high ethanol resistance regardless of the presence or absence of Msn2 (FIG. 15B). These data provide compelling physiological evidence that the Mig3 effect is Msn2-independent.

Figure 17:
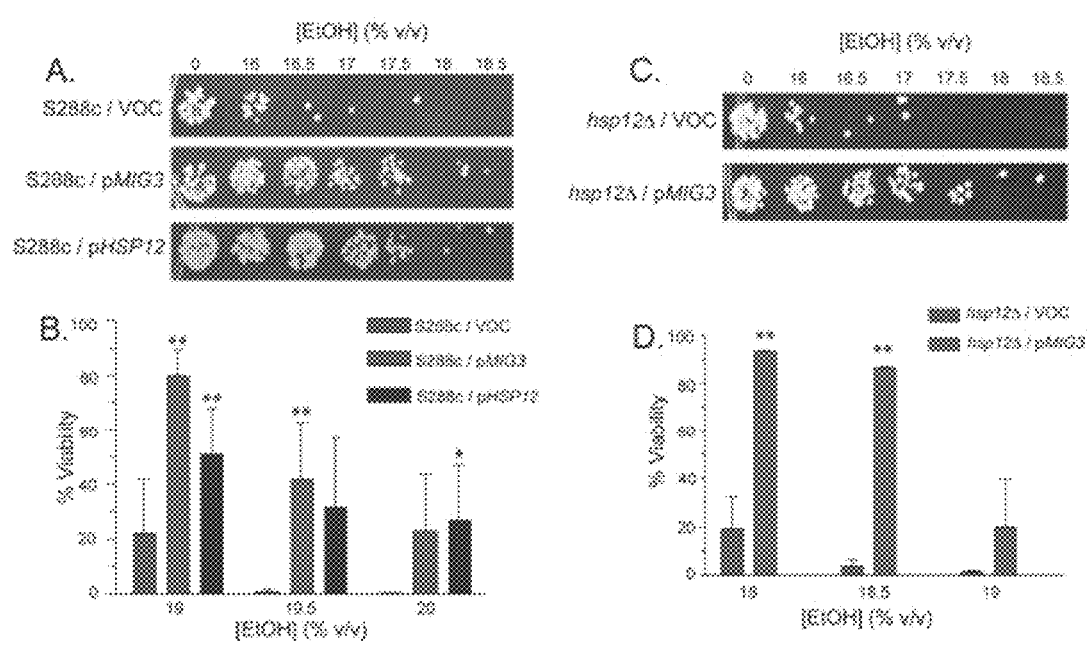
FIG. 17 depicts data showing that over-expression of Mig3 confers ethanol tolerance even in the absence of Hsp12. A) A representative experiment showing strain basal tolerances to 2 hr exposure of indicated ethanol doses in BY4741 containing galactose-inducible Mig3 plasmid, Hsp12 plasmid, or a control vector (pEGH). B) Viability of over-expression strains scored for a 2 hour exposure to the indicated doses of ethanol. C) A representative experiment showing the increased ethanol tolerance of a hsp12Δ strain containing the Mig3 plasmid compared to the control vector (pEGH). D) Viability of the strains shown in 'C.' Where shown, error bars indicate standard deviation of biological triplicates. (*=p<0.05, **=p<0.01, t-test).

To further understand the effects of Mig3 over-expression on cellular physiology, global gene expression in the MIG3 over-expressing strain was measured. Surprisingly, Mig3 over-expression resulted in a large number of gene expression changes. Two hundred and nine genes were significantly induced (FDR=0.01) and 199 genes were significantly repressed when Mig3 was over-expressed (data not shown). These results are consistent with the known ability of both Mig1 and Mig2 proteins to function as both activators and repressors. The most highly induced gene was HSP12, which encodes a heat shock protein with a known role in thermotolerance. Because the mechanisms for thermotolerance and ethanol tolerance are thought to be partially overlapping, the inventors tested whether HSP12 over-expression could increase ethanol resistance by itself. Indeed, over-expression of Hsp12 was able to confer higher ethanol tolerance in S288c (FIGS. 17A,B). Next the inventors tested whether Mig3 over-expression could still increase ethanol tolerance even in a strain lacking Hsp12. Intriguingly, Mig3 over-expression in a hsp12Δ mutant was still able to confer high levels of ethanol tolerance (FIGS. 17C,D), suggesting that additional Mig3-regulated genes contribute to the increased ethanol tolerance. Genes induced by Mig3 were strongly enriched for transposition, and were also enriched for pseudouridine synthesis and proteolysis. While not enriched several stress related genes in addition to HSP12 were induced, including ARO9, ARO10, YGP1, MOH1, MSC1, FMP45, AMS1, PAI3, GPM2, SPI1, SUE1, HSP42, CTT1, and DDR48. Induction of these stress genes may contribute to the high ethanol tolerance of the Mig3 over-expressing strain.

In contrast to the Mig3-activated genes, genes repressed by Mig3 were enriched for carbohydrate metabolism, cellular respiration, and hexose transport, suggesting that Mig3 may still play a role in glucose repression. Importantly, the genes affected by Mig3 over-expression show poor overlap with those known to be regulated by Msn2. These data confirm that the Mig3 and Msn2 regulons are indeed distinct. To further study the role of Mig3 in yeast physiology, the inventors analyzed both basal gene expression and the ethanol response in a YPS163 mig3Δ strain. In S288c, no genes were differentially expressed under either condition (FDR=0.01). In contrast, 320 genes had higher basal gene expression in the wild-type strain relative to the mig3Δ strain, consistent with Mig3-mediated activation. These genes were enriched for nitrogen metabolism, ATP biosynthesis, proton transport, electron transport chain, and aerobic respiration. Another 352 genes had higher basal gene expression in the mig3Δ strain relative to the wild-strain; these genes were enriched for mitochondrial translation, metabolism of energy reserves, alcohol catabolism, and glycolysis. Additionally, 181 genes had defective induction by ethanol in the mig3Δ strain. These genes were enriched for transposons, cell cycle, and mitochondrial translation. The 391 genes with defective repression by ethanol in the mig3Δ strain were enriched for hexose transport, electron transport chain, iron ion homeostasis, and ATP synthesis. The results from these gene expression experiments suggest a novel role for Mig3 in energy metabolism that is absent in the lab strain.

These results demonstrate the power of using natural variation and multiple strain backgrounds to identify novel functions for uncharacterized genes. This strategy led the inventors to identify a novel role for Mig3 in ethanol tolerance. Specifically, the inventors showed that over-expression of this transcription factor increases ethanol resistance. Additionally, transcriptional profiling of the Mig3 over-expressing strain identified hundreds of Mig3-regulated genes, which further increases our understanding of the effect of this transcription factor on yeast physiology.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Solomon, B. D. (2010) Biofuels and sustainability Ann NY Acad Sci 1185:119-134.
2. Alper, H., et al. (2006) Engineering yeast transcription machinery for improved ethanol tolerance and production. Science 314:1565-1568.

3. Stanley, D., et al. (2010) The ethanol stress response and ethanol tolerance of *Saccharomyces cerevisiae*. J Appl Microbiol 109:13-24.
4. Fujita, K., Matsuyama, A., Kobayashi, Y., Iwahashi, H. (2006) The genome-wide screening of yeast deletion mutants to identify the genes required for tolerance to ethanol and other alcohols. FEMS Yeast Res 6:744-750.
5. Teixeira, M. C., et al. (2009) Genome-wide identification of *Saccharomyces cerevisiae* genes required for maximal tolerance to ethanol. Appl. Environ. Microbiol. 75:5761-5772.
6. van Voorst, F., et al. (2006) Genome-wide identification of genes required for growth of *Saccharomyces cerevisiae* under ethanol stress. Yeast 23:351-359.
7. Yoshikawa, K., et al. (2009) Comprehensive phenotypic analysis for identification of genes affecting growth under ethanol stress in *Saccharomyces cerevisiae*. FEMS Yeast Res 9:32-44.
8. Kubota, S., et al. (2004) Effect of ethanol on cell growth of budding yeast: genes that are important for cell growth in the presence of ethanol. Biosci. Biotechnol. Biochem. 68:968-972.
9. Alexandre, H., Ansanay-Galeote, V., Dequin, S., Blondin, B. (2001) Global gene expression during short-term ethanol stress in *Saccharomyces cerevisiae*. FEBS Lett 498:98-103.
10. Fujita, K., Matsuyama, A., Kobayashi, Y., Iwahashi, H. (2004) Comprehensive gene expression analysis of the response to straight-chain alcohols in *Saccharomyces cerevisiae* using cDNA microarray. J Appl Microbiol 97:57-67.
11. Chandler, M., Stanley, G. A., Rodgers, P., Chambers, P. (2004) A genomic approach to defining the ethanol stress response in the yeast *Saccharomyces cerevisiae*. Ann Microbiol 54:427-545.
12. Hirasawa, T., et al. (2007) Identification of target genes conferring ethanol stress tolerance to *Saccharomyces cerevisiae* based on DNA microarray data analysis. J Biotechnol 131:34-44.
13. Berry, D. B., Gasch, A. P. (2008) Stress-activated genomic expression changes serve a preparative role for impending stress in yeast. Mol Biol Cell 19:4580-4587.
14. Rossignol, T., Dulau, L., Julien, A., Blondin, B. (2003) Genome-wide monitoring of wine yeast gene expression during alcoholic fermentation. Yeast 20:1369-1385.
15. Wu, H., et al. (2006) Global gene expression analysis of yeast cells during sake brewing. Appl Environ Microbiol 72:7353-7358.
16. Cavalieri, D., Townsend, J. P., Hartl, D. L. (2000) Manifold anomalies in gene expression in a vineyard isolate of *Saccharomyces cerevisiae* revealed by DNA microarray analysis. Proc Natl Acad Sci USA 97:12369-12374.
17. Fay, J. C., McCullough, H. L., Sniegowski, P. D., Eisen, M. B. (2004) Population genetic variation in gene expression is associated with phenotypic variation in *Saccharomyces cerevisiae*. Genome Biol 5:R26.
18. Kvitek, D. J., Will, J. L., Gasch, A. P. (2008) Variations in stress sensitivity and genomic expression in diverse *S. cerevisiae* isolates. PLoS Genet. 4:e1000223.
19. Mortimer, R. K., Johnston, J. R. (1986) Genealogy of principal strains of the yeast genetic stock center. Genetics 113:35-43.
20. Gasch, A. P., et al. (2000) Genomic expression programs in the response of yeast cells to environmental changes. Mol Biol Cell 11:4241-4257.
21. Gaisne, M., Becam, A. M., Verdiere, J., Herbert, C. J. (1999) A 'natural' mutation in *Saccharomyces cerevisiae* strains derived from S288c affects the complex regulatory gene HAP1 (CYP1). Curr Genet. 36:195-200.
22. Watanabe, M., Watanabe, D., Akao, T., Shimoi, H. (2009) Overexpression of MSN2 in a sake yeast strain promotes ethanol tolerance and increases ethanol production in sake brewing. J Biosci Bioeng 107:516-518.
23. You, K. M., Rosenfield, C. L., Knipple, D. C. (2003) Ethanol tolerance in the yeast *Saccharomyces cerevisiae* is dependent on cellular oleic acid content. Appl Environ Microbiol 69:1499-1503.
24. Meaden, P. G., et al. (1999) Endocytosis and vacuolar morphology in *Saccharomyces cerevisiae* are altered in response to ethanol stress or heat shock. Yeast 15:1211-1222.
25. Lucero, P., Penalver, E., Moreno, E., Lagunas, R. (2000) Internal trehalose protects endocytosis from inhibition by ethanol in *Saccharomyces cerevisiae*. Appl. Environ. Microbiol. 66:4456-4461.
26. Singer, M. A., Lindquist, S. (1998) Multiple effects of trehalose on protein folding in vitro and in vivo. Mol Cell 1:639-648.
27. Sajbidor, J., Ciesarova, Z., Smogrovicova, D. (1995) Influence of ethanol on the lipid content and fatty acid composition of *Saccharomyces cerevisiae*. Folia Microbiol (Praha) 40:508-510.
28. Walker-Caprioglio, H. M., Casey, W. M., Parks, L. W. (1990) *Saccharomyces cerevisiae* membrane sterol modifications in response to growth in the presence of ethanol. Appl Environ Microbiol 56:2853-2857.
29. Lu, A., Hirsch, J. P. (2005) Cyclic AMP-independent regulation of protein kinase A substrate phosphorylation by Kelch repeat proteins. Eukaryot. Cell 4:1794-1800.
30. Sopko, R., et al. (2006) Mapping pathways and phenotypes by systematic gene overexpression. Mol Cell 21:319-330.
31. Gasch, A. P. (2002) Yeast genomic expression studies using DNA microarrays. Methods Enzymol 350:393-414.
Gentleman R. C., et al. (2004) Bioconductor: open software development for computational biology and bioinformatics. Genome Biol 5:R80
32. Lyne, R., et al. (2003) Whole-genome microarrays of fission yeast: characteristics, accuracy, reproducibility, and processing of array data. BMC Genomics 4:27.
33. Smyth, G. K. (2004) Linear models and empirical bayes methods for assessing differential expression in microarray experiments. Stat Appl Genet Mol Biol 3:Article3.
34. Storey, J. D., Tibshirani, R. (2003) Statistical significance for genomewide studies. Proc Natl Acad Sci USA 100:9440-9445.
35. Eisen, M. B., Spellman, P. T., Brown, P. O., Botstein, D. (1998) Cluster analysis and display of genome-wide expression patterns. Proc Natl Acad Sci USA 95:14863-14868.
36. Boyle, E. I., et al. (2004) GO::TermFinder—open source software for accessing Gene Ontology information and finding significantly enriched Gene Ontology terms associated with a list of genes. Bioinformatics 20:3710-3715.
37. Sherman, F. (2002) Getting started with yeast. Methods Enzymol 350:3-41.
38. Bligh, E. G., Dyer, W. J. (1959) A rapid method of total lipid extraction and purification. Can J Biochem Physiol 37:911-917.
39. Christie, W. W. (1989) Gas chromatography and lipids: a practical guide. Oily Press 36-38.
Berry, D. B., and A. P. Gasch. 2008. Stress-activated genomic expression changes serve a preparative role for impending stress in yeast. Mol Biol Cell 19:4580-4587.

Dubacq, C., A. Chevalier, and C. Mann. 2004. The protein kinase Snf1 is required for tolerance to the ribonucleotide reductase inhibitor hydroxyurea. Mol Cell Biol 24:2560-2572.

Gasch, A. P. 2002. Yeast genomic expression studies using DNA microarrays. Methods Enzymol 350:393-414.

Gonnet, G. H., M. A. Cohen, and S. A. Benner. 1992. Exhaustive matching of the entire protein sequence database. Science 256:1443-1445.

Lewis, J. A., I. M. Elkon, M. A. McGee, A. J. Higbee, and A. P. Gasch. 2010. Exploiting natural variation in *Saccharomyces cerevisiae* to identify genes for increased ethanol resistance. Genetics 186:1197-1205.

Lutfiyya, L. L., V. R. Iyer, J. DeRisi, M. J. DeVit, P. O. Brown, and M. Johnston. 1998. Characterization of three related glucose repressors and genes they regulate in *Saccharomyces cerevisiae*. Genetics 150:1377-1391.

Lyne, R., G. Burns, J. Mata, C. J. Penkett, G. Rustici, D. Chen, C. Langford, D. Vetrie, and J. Bahler. 2003. Whole-genome microarrays of fission yeast: characteristics, accuracy, reproducibility, and processing of array data. BMC Genomics 4:27.

Piper, P. W. 1995. The heat shock and ethanol stress responses of yeast exhibit extensive similarity and functional overlap. FEMS Microbiol. Lett. 134:121-127.

Praekelt, U. M., and P. A. Meacock. 1990. HSP12, a new small heat shock gene of *Saccharomyces cerevisiae*: analysis of structure, regulation and function. Mol Gen Genet. 223:97-106.

Sopko, R., D. Huang, N. Preston, G. Chua, B. Papp, K. Kafadar, M. Snyder, S. G. Oliver, M. Cyert, T. R. Hughes, C. Boone, and B. Andrews. 2006. Mapping pathways and phenotypes by systematic gene overexpression. Mol Cell 21:319-330.

Valadi, H., A. Valadi, R. Ansell, L. Gustafsson, L. Adler, J. Norbeck, and A. Blomberg. 2004. NADH-reductive stress in *Saccharomyces cerevisiae* induces the expression of the minor isoform of glyceraldehyde-3-phosphate dehydrogenase (TDH1). Curr Genet. 45:90-95.

Westholm, J. O., N. Nordberg, E. Muren, A. Ameur, J. Komorowski, and H. Ronne. 2008. Combinatorial control of gene expression by the three yeast repressors Mig1, Mig2 and Mig3. BMC Genomics 9:601.

Open Biosystems 2008. Yeast GST Manual, Document SS051497, in Yeast GST Fusion Collection and Strains; Catalog numbers YSC4423 & YSC4515. Huntsville, Ala.

Mitchell, D. A., T. K. Marshall, and R. J. Deschenes 1993. Vectors for the inducible overexpression of glutathione S-transferase fusion proteins in yeast. Yeast 9:715-722.

---

What is claimed is:

1. An isolated nucleic acid comprising a nucleotide sequence encoding SEQ ID NO:3, wherein expression thereof in recombinant yeast provides increased ethanol tolerance in said yeast relative to a control yeast lacking expression of the isolated nucleic acid.

2. The isolated nucleic acid of claim 1, further comprising a heterologous promoter operably linked to said isolated nucleic acid.

3. The isolated nucleic acid according to claim 2, wherein said heterologous promoter is the ACT1, PGK1, TDH3, TEF1, TEF2, GAL4, CUP1, PHO5, or tetO7 promoter.

4. The isolated nucleic acid according to claim 2, wherein said heterologous promoter is an inducible heterologous promoter and increased ethanol tolerance in the recombinant yeast is conferred by induction of the inducible heterologous promoter.

5. The isolated nucleic acid according to claim 4, wherein said inducible heterologous promoter is the GAL4, CUP1, PHO5, or tetO7 promoter.

6. A recombinant vector comprising the isolated nucleic acid of claim 1.

7. A recombinant yeast comprising the isolated nucleic acid of claim 1.

8. The recombinant yeast of claim 7, wherein the recombinant yeast is of the genus *Saccharomyces*.

9. The recombinant yeast of claim 7, wherein the recombinant yeast is of the species *Saccharomyces cerevisiae*.

10. The recombinant yeast of claim 7, wherein the isolated nucleic acid is a portion of an extrachromosomal vector stably maintained in the recombinant yeast.

11. The recombinant yeast of claim 7, wherein the isolated nucleic acid is integrated into a chromosome of the recombinant yeast.

12. The recombinant yeast according to claim 7, wherein said recombinant yeast is of the *Saccharomyces cerevisiae* strain CEN.PK, PE-2, BG-1, CAT-1, SA-1, VR-1 or JAY270.

13. A yeast inoculum, comprising: (a) a recombinant yeast of claim 7; and (b) a culture medium.

14. A method for producing ethanol from a recombinant yeast, comprising: (a) culturing under ethanol-producing conditions a recombinant yeast comprising an isolated nucleic acid comprising:
(i) a nucleotide sequence encoding the Elo1 polypeptide of SEQ ID NO:1 or a polypeptide having at least 90% identity to SEQ ID NO:1 that is capable of enzyme elongation of fatty acids; or (ii) a nucleotide sequence encoding the Mig3 polypeptide of SEQ ID NO:3, a polypeptide having at least 90% identity to SEQ ID NO:3, or a nucleotide sequence which hybridizes to SEQ ID NO:6 at highly stringent conditions of 1×SSC, at about 65-70° C. followed by one or more washes in 0.3×SSC, at about 65-70° C., or to a fully complementary nucleotide sequence of SEQ ID NO:6, wherein expression in a recombinant yeast of said isolated nucleic acid provides increased ethanol tolerance in the recombinant yeast relative to a control yeast lacking expression of the isolated nucleic acid; and (b) isolating ethanol produced by said recombinant yeast.

15. The method according to claim 14, wherein at least a portion of said culturing takes place in a culture medium having an ethanol concentration of greater than about 15% (v/v).

16. The method according to claim 14, wherein at least a portion of said culturing takes place in a culture medium having an ethanol concentration of greater than about 20% (v/v).

17. A method for providing a recombinant yeast useful in ethanol production, comprising introducing into an isolated yeast an isolated nucleic acid according to claim 1, thereby providing a recombinant yeast capable of increased ethanol tolerance relative to a control yeast lacking said isolated nucleic acid.

18. The method of claim 17, wherein the recombinant yeast is *Saccharomyces cerevisiae*.

19. A recombinant yeast provided by the method according to claim 17.

20. A recombinant *Saccharomyces cerevisiae* strain designated BY4741/pEGH(ELO1).

21. A recombinant *Saccharomyces cerevisiae* strain designated BY4741/pEGH(MIG3).

* * * * *

SEQUENCE LISTING

```
<160> NUMBER OF SEQ ID NOS: 6

<210> SEQ ID NO 1
<211> LENGTH: 310
<212> TYPE: PRT
<213> ORGANISM: Saccharomyces cerevisiae

<400> SEQUENCE: 1

Met Val Ser Asp Trp Lys Asn Phe Cys Leu Glu Lys Ala Ser Arg Phe
1               5                   10                  15

Arg Pro Thr Ile Asp Arg Pro Phe Phe Asn Ile Tyr Leu Trp Asp Tyr
            20                  25                  30

Phe Asn Arg Ala Val Gly Trp Ala Thr Ala Gly Arg Phe Gln Pro Lys
        35                  40                  45

Asp Phe Glu Phe Thr Val Gly Lys Gln Pro Leu Ser Glu Pro Arg Pro
    50                  55                  60

Val Leu Leu Phe Ile Ala Met Tyr Tyr Val Val Ile Phe Gly Gly Arg
65                  70                  75                  80

Ser Leu Val Lys Ser Cys Lys Pro Leu Lys Leu Arg Phe Ile Ser Gln
                85                  90                  95

Val His Asn Leu Met Leu Thr Ser Val Ser Phe Leu Trp Leu Ile Leu
            100                 105                 110

Met Val Glu Gln Met Leu Pro Ile Val Tyr Arg His Gly Leu Tyr Phe
        115                 120                 125

Ala Val Cys Asn Val Glu Ser Trp Thr Gln Pro Met Glu Thr Leu Tyr
    130                 135                 140

Tyr Leu Asn Tyr Met Thr Lys Phe Val Glu Phe Ala Asp Thr Val Leu
145                 150                 155                 160

Met Val Leu Lys His Arg Lys Leu Thr Phe Leu His Thr Tyr His His
                165                 170                 175

Gly Ala Thr Ala Leu Leu Cys Tyr Asn Gln Leu Val Gly Tyr Thr Ala
            180                 185                 190
```

```
Val Thr Trp Val Pro Val Thr Leu Asn Leu Ala Val His Val Leu Met
        195                 200                 205

Tyr Trp Tyr Tyr Phe Leu Ser Ala Ser Gly Ile Arg Val Trp Trp Lys
210                 215                 220

Ala Trp Val Thr Arg Leu Gln Ile Val Gln Phe Met Leu Asp Leu Ile
225                 230                 235                 240

Val Val Tyr Tyr Val Leu Tyr Gln Lys Ile Val Ala Ala Tyr Phe Lys
                245                 250                 255

Asn Ala Cys Thr Pro Gln Cys Glu Asp Cys Leu Gly Ser Met Thr Ala
            260                 265                 270

Ile Ala Ala Gly Ala Ala Ile Leu Thr Ser Tyr Leu Phe Leu Phe Ile
        275                 280                 285

Ser Phe Tyr Ile Glu Val Tyr Lys Arg Gly Ser Ala Ser Gly Lys Lys
    290                 295                 300

Lys Ile Asn Lys Asn Asn
305                 310

<210> SEQ ID NO 2
<211> LENGTH: 933
<212> TYPE: DNA
<213> ORGANISM: Saccharomyces cerevisiae

<400> SEQUENCE: 2
atggtaagtg attggaaaaa tttttgcctc gagaaagcct ctaggtttcg cccaacaata      60
gataggcctt tttttaatat ttatttgtgg gactatttca atcgtgcggt tgggtgggcc     120
actgcaggtc gcttccagcc aaaggatttt gagtttaccg ttgggaagca gcctttgagt     180
gaacctcgtc cggtactgct tttattgcc atgtattatg tggttatatt tggcgggagg      240
tccctggtaa agtcatgtaa acctctcaag ttgagattta tttctcaagt ccataacttg     300
atgttgactt ctgtttcctt tttatggttg attttgatgg tggaacagat gctacccata     360
gtgtatcgcc atgggctgta ttttgctgtt tgtaatgttg aatcgtggac gcaaccgatg     420
gagacattat attatctcaa ctatatgaca aagtttgtgg agttcgcaga cactgtcttg     480
atggtgttga acatagaaa gttgactttc ctacatacat accatcatgg tgctacagct     540
ttactgtgct ataatcaatt ggttggttac acagcagtta catgggttcc tgtcacctta     600
aacttagctg ttcacgttct tatgtattgg tattatttcc tttctgctag cggaattcgt     660
gtttggtgga aagcctgggt tacaagacta caaattgtgc agttcatgct tgatctcatt     720
gtcgtttatt acgtgcttta tcagaagatt gttgctgcat atttcaaaaa tgcttgtact     780
ccacagtgtg aggattgctt aggttcaatg acggctattg ctgctggtgc agccattctt     840
acatcctact tgtttttgtt catctctttc tatattgagg tttacaaacg tggaagtgct     900
agtggtaaga agaagatcaa caaaaacaat taa                                  933

<210> SEQ ID NO 3
<211> LENGTH: 377
<212> TYPE: PRT
<213> ORGANISM: Saccharomyces cerevisiae

<400> SEQUENCE: 3

Met Asn Tyr Leu Arg Asp Arg Phe Pro Pro Asp Asn Asp Gln Arg Pro
1               5                   10                  15

Phe Arg Cys Glu Ile Cys Ser Arg Gly Phe His Arg Leu Glu His Lys
            20                  25                  30

Lys Arg His Gly Arg Thr His Thr Gly Glu Lys Pro His Lys Cys Thr
        35                  40                  45
```

Val Gln Gly Cys Pro Lys Ser Phe Ser Arg Ser Asp Glu Leu Lys Arg
            50                  55                  60

His Leu Arg Thr His Thr Lys Gly Val Gln Arg Arg Ile Lys Lys
 65                  70                  75                  80

Gly Ser Arg Lys Thr Val Val Asn Thr Ala Thr Ala Ala Pro Thr Thr
                85                  90                  95

Phe Asn Glu Asn Thr Gly Val Ser Leu Thr Gly Ile Gly Gln Ser Lys
            100                 105                 110

Val Pro Pro Ile Leu Ile Ser Val Ala Gln Asn Cys Asp Asp Val Asn
        115                 120                 125

Ile Arg Asn Thr Gly Asn Asn Asn Gly Ile Val Glu Thr Gln Ala Pro
    130                 135                 140

Ala Ile Leu Val Pro Val Ile Asn Ile Pro Asn Asp Pro His Pro Ile
145                 150                 155                 160

Pro Ser Ser Leu Ser Thr Thr Ser Ile Thr Ser Ile Ala Ser Val Tyr
                165                 170                 175

Pro Ser Thr Ser Pro Phe Gln Tyr Leu Lys Ser Gly Phe Pro Glu Asp
            180                 185                 190

Pro Ala Ser Thr Pro Tyr Val His Ser Ser Gly Ser Ser Leu Ala Leu
        195                 200                 205

Gly Glu Leu Ser Ser Asn Ser Ser Ile Phe Ser Lys Ser Arg Arg Asn
    210                 215                 220

Leu Ala Ala Met Ser Gly Pro Asp Ser Leu Ser Ser Ser Lys Asn Gln
225                 230                 235                 240

Ser Ser Ala Ser Leu Leu Ser Gln Thr Ser His Pro Ser Lys Ser Phe
                245                 250                 255

Ser Arg Pro Pro Thr Asp Leu Ser Pro Leu Arg Arg Ile Met Pro Ser
            260                 265                 270

Val Asn Thr Gly Asp Met Glu Ile Ser Arg Thr Val Ser Val Ser Ser
        275                 280                 285

Ser Ser Ser Ser Leu Thr Ser Val Thr Tyr Asp Thr Ala Ala Lys
    290                 295                 300

Asp Met Gly Met Gly Ile Phe Phe Asp Arg Pro Val Thr Gln Lys
305                 310                 315                 320

Ala Cys Arg Ser Asn His Lys Tyr Lys Val Asn Ala Val Ser Arg Gly
                325                 330                 335

Arg Gln His Glu Arg Ala Gln Phe His Ile Ser Gly Asp Asp Glu Asp
            340                 345                 350

Ser Asn Val His Arg Gln Glu Ser Arg Ala Ser Asn Thr Ser Pro Asn
        355                 360                 365

Val Ser Leu Pro Pro Ile Lys Ser Ile
    370                 375

<210> SEQ ID NO 4
<211> LENGTH: 382
<212> TYPE: PRT
<213> ORGANISM: Saccharomyces cerevisiae

<400> SEQUENCE: 4

Met Pro Lys Lys Gln Thr Asn Phe Pro Val Asp Asn Glu Asn Arg Pro
1               5                   10                  15

Phe Arg Cys Asp Thr Cys His Arg Gly Phe His Arg Leu Glu His Lys
            20                  25                  30

Lys Arg His Leu Arg Thr His Thr Gly Glu Lys Pro His Cys Ala
        35                  40                  45

Phe Pro Gly Cys Gly Lys Ser Phe Ser Arg Ser Asp Glu Leu Lys Arg
            50                  55                  60

His Met Arg Thr His Thr Gly Gln Ser Gln Arg Leu Lys Lys Ala
 65                  70                  75                  80

Ser Val Gln Lys Gln Glu Phe Leu Thr Val Ser Gly Ile Pro Thr Ile
                85                  90                  95

Ala Ser Gly Val Met Ile His Gln Pro Ile Pro Gln Val Leu Pro Ala
               100                 105                 110

Asn Met Ala Ile Asn Val Gln Ala Val Asn Gly Gly Asn Ile Ile His
           115                 120                 125

Ala Pro Asn Ala Val His Pro Met Val Ile Pro Ile Met Ala Gln Pro
130                 135                 140

Ala Pro Ile His Ala Ser Ala Ser Phe Gln Pro Ala Thr Ser Pro
145                 150                 155                 160

Met Pro Ile Ser Thr Tyr Thr Pro Val Pro Ser Gln Ser Phe Thr Ser
                165                 170                 175

Phe Gln Ser Ser Ile Gly Ser Ile Gln Ser Asn Ser Asp Val Ser Ser
                180                 185                 190

Ile Phe Ser Asn Met Asn Val Arg Val Asn Thr Pro Arg Ser Val Pro
            195                 200                 205

Asn Ser Pro Asn Asp Gly Tyr Leu His Gln His Ile Pro Gln Gln
210                 215                 220

Tyr Gln His Gln Thr Ala Ser Pro Ser Val Ala Lys Gln Gln Lys Thr
225                 230                 235                 240

Phe Ala His Ser Leu Ala Ser Ala Leu Ser Thr Leu Gln Lys Arg Thr
                245                 250                 255

Pro Val Ser Ala Pro Ser Thr Thr Ile Glu Ser Pro Ser Pro Ser
            260                 265                 270

Asp Ser Ser His Thr Ser Ala Ser Ser Ala Ile Ser Leu Pro Phe
            275                 280                 285

Ser Asn Ala Pro Ser Gln Leu Ala Val Ala Lys Glu Leu Glu Ser Val
290                 295                 300

Tyr Leu Asp Ser Asn Arg Tyr Thr Thr Lys Thr Arg Arg Glu Arg Ala
305                 310                 315                 320

Lys Phe Glu Ile Pro Glu Glu Gln Glu Glu Asp Thr Asn Asn Ser Ser
                325                 330                 335

Ser Gly Ser Asn Glu Glu Glu His Glu Ser Leu Asp His Glu Ser Ser
            340                 345                 350

Lys Ser Arg Lys Lys Leu Ser Gly Val Lys Leu Pro Pro Val Arg Asn
            355                 360                 365

Leu Leu Lys Gln Ile Asp Val Phe Asn Gly Pro Lys Arg Val
370                 375                 380

<210> SEQ ID NO 5
<211> LENGTH: 503
<212> TYPE: PRT
<213> ORGANISM: Saccharomyces cerevisiae

<400> SEQUENCE: 5

Met Gln Ser Pro Tyr Pro Met Thr Gln Val Ser Asn Val Asp Asp Gly
 1               5                  10                  15

Ser Leu Leu Lys Glu Ser Lys Ser Lys Ser Lys Val Ala Ala Lys Ser
                20                  25                  30

Glu Ala Pro Arg Pro His Ala Cys Pro Ile Cys His Arg Ala Phe His
            35                  40                  45

```
Arg Leu Glu His Gln Thr Arg His Met Arg Ile His Thr Gly Glu Lys
     50                  55                  60

Pro His Ala Cys Asp Phe Pro Gly Cys Val Lys Arg Phe Ser Arg Ser
 65                  70                  75                  80

Asp Glu Leu Thr Arg His Arg Arg Ile His Thr Asn Ser His Pro Arg
                 85                  90                  95

Gly Lys Arg Gly Arg Lys Lys Lys Val Val Gly Ser Pro Ile Asn Ser
            100                 105                 110

Ala Ser Ser Ser Ala Thr Ser Ile Pro Asp Leu Asn Thr Ala Asn Phe
        115                 120                 125

Ser Pro Pro Leu Pro Gln Gln His Leu Ser Pro Leu Ile Pro Ile Ala
    130                 135                 140

Ile Ala Pro Lys Glu Asn Ser Ser Arg Ser Ser Thr Arg Lys Gly Arg
145                 150                 155                 160

Lys Thr Lys Phe Glu Ile Gly Glu Ser Gly Gly Asn Asp Pro Tyr Met
                165                 170                 175

Val Ser Ser Pro Lys Thr Met Ala Lys Ile Pro Val Ser Val Lys Pro
            180                 185                 190

Pro Pro Ser Leu Ala Leu Asn Asn Met Asn Tyr Gln Thr Ser Ser Ala
        195                 200                 205

Ser Thr Ala Leu Ser Ser Leu Ser Asn Ser His Ser Gly Ser Arg Leu
    210                 215                 220

Lys Leu Asn Ala Leu Ser Ser Leu Gln Met Met Thr Pro Ile Ala Ser
225                 230                 235                 240

Ser Ala Pro Arg Thr Val Phe Ile Asp Gly Pro Glu Gln Lys Gln Leu
                245                 250                 255

Gln Gln Gln Gln Asn Ser Leu Ser Pro Arg Tyr Ser Asn Thr Val Ile
            260                 265                 270

Leu Pro Arg Pro Arg Ser Leu Thr Asp Phe Gln Gly Leu Asn Asn Ala
        275                 280                 285

Asn Pro Asn Asn Asn Gly Ser Leu Arg Ala Gln Thr Gln Ser Ser Val
    290                 295                 300

Gln Leu Lys Arg Pro Ser Ser Val Leu Ser Leu Asn Asp Leu Leu Val
305                 310                 315                 320

Gly Gln Arg Asn Thr Asn Glu Ser Asp Ser Asp Phe Thr Thr Gly Gly
                325                 330                 335

Glu Asp Glu Glu Asp Gly Leu Lys Asp Pro Ser Asn Ser Ser Ile Asp
            340                 345                 350

Asn Leu Glu Gln Asp Tyr Leu Gln Glu Gln Ser Arg Lys Lys Ser Lys
        355                 360                 365

Thr Ser Thr Pro Thr Thr Met Leu Ser Arg Ser Thr Ser Gly Thr Asn
    370                 375                 380

Leu His Thr Leu Gly Tyr Val Met Asn Gln Asn His Leu His Phe Ser
385                 390                 395                 400

Ser Ser Ser Pro Asp Phe Gln Lys Glu Leu Asn Asn Arg Leu Leu Asn
                405                 410                 415

Val Gln Gln Gln Gln Glu Gln His Thr Leu Leu Gln Ser Gln Asn
            420                 425                 430

Thr Ser Asn Gln Ser Gln Asn Gln Asn Gln Met Met Ala Ser
        435                 440                 445

Ser Ser Ser Leu Ser Thr Thr Pro Leu Leu Leu Ser Pro Arg Val Asn
    450                 455                 460

Met Ile Asn Thr Ala Ile Ser Thr Gln Gln Thr Pro Ile Ser Gln Ser
```

```
                     465              470              475              480
Asp Ser Gln Val Gln Glu Leu Glu Thr Leu Pro Pro Ile Arg Ser Leu
                    485                       490                  495
Pro Leu Pro Phe Pro His Met
                500

<210> SEQ ID NO 6
<211> LENGTH: 1185
<212> TYPE: DNA
<213> ORGANISM: Saccharomyces cerevisiae

<400> SEQUENCE: 6
atgaattacc tgcgagatag atttcctccg gataatgacc aaagacccct tagatgtgaa    60
atttgttcac gaggtttcca cagacttgaa cataaaaaaa ggcacggaag aacgcacact   120
ggcgagaagc ctcacaaatg taccgttcag ggctgtccga aaagcttcag ccgaagcgat   180
gaactaaaaa gacatttgag gacacatact aaaggcgtcc aaaggcgcag aataaaatcc   240
aagggctcgc gaaaaaccgt tgtgaatact gctaccgccg ccctaccac cttcaatgaa    300 aacactggtg tttcgctcac ggggataggt caatctaaag tgccacctat tcttatctcc   360
gttgctcaga attgcgatga cgtgaatata cgaaatactg gaaataataa tggcattgtg   420
gagacacagg cacctgcaat tttagtgcct gtgataaata ttccaaatga ccctcatccg   480
attccaagta gcctctccac tacttctatc acctccattg catcagtata tccctctact   540
tctccattcc agtacctgaa aagcgggttt cctgaagatc ctgcatctac accgtatgta   600
cattcgtccg gaagttcttt agccctgggt gaattgtctt caaactcctc tatattttcg   660
aaatctagga ggaatttggc cgccatgagt ggtcctgatt ctttgagtag ttctaaaaac   720
caatccagtg cttcgcttct ttctcaaact tcacatccat caaagagctt ttcaagaccg   780
ccaacagact taagtcctct gcgaagaatc atgccttctg taaacacagg agacatggaa   840
atttcaagga cagtatccgt ttcgagcagt tcatcatcac tcacttctgt tacgtatgat   900
gacaccgcgg ctaaagacat gggcatggga atattttttg ataggccacc tgtaacacag   960
aaagcttgca ggagcaatca taagtacaag gttaatgctg ttagcagagg gagacaacat  1020
gaaagggcac aatttcatat atctggagat gatgaggaca gtaacgttca ccgccaagaa  1080
tcaagagcat ccaacacaag tcccaatgta tcattgcctc cgataaagag cattttgcga  1140
caaattgata atttcaacag tgctccttct tacttcagta aataa                  1185
```